US009638668B2

(12) United States Patent
Makino et al.

(10) Patent No.: US 9,638,668 B2
(45) Date of Patent: May 2, 2017

(54) SURFACE PROPERTY INSPECTION APPARATUS, SURFACE PROPERTY INSPECTION SYSTEM, AND SURFACE PROPERTY INSPECTION METHOD

(71) Applicant: SINTOKOGIO, LTD., Nagoya-shi, Aichi (JP)

(72) Inventors: Yoshiyasu Makino, Toyokawa (JP); Hideaki Kaga, Toyokawa (JP)

(73) Assignee: SINTOKOGIO, LTD., Aichi (JP)

( * ) Notice: Subject to any disclaimer, the term of this patent is extended or adjusted under 35 U.S.C. 154(b) by 118 days.

(21) Appl. No.: 14/707,600

(22) Filed: May 8, 2015

(65) Prior Publication Data

US 2015/0241391 A1 Aug. 27, 2015

Related U.S. Application Data

(63) Continuation of application No. PCT/JP2014/054100, filed on Feb. 14, 2014.

(30) Foreign Application Priority Data

May 30, 2013 (JP) ................................. 2013-113694

(51) Int. Cl.
*G01N 27/82* (2006.01)
*G01N 27/72* (2006.01)
(Continued)

(52) U.S. Cl.
CPC ........... *G01N 27/9046* (2013.01); *C21D 7/06* (2013.01); *C21D 11/00* (2013.01); *G01N 27/9006* (2013.01)

(58) Field of Classification Search
CPC .................................. G01R 33/12; G01N 27/80
(Continued)

(56) References Cited

U.S. PATENT DOCUMENTS 3,020,745 A 2/1962 Sielicki
5,485,084 A 1/1996 Duncan et al.
(Continued)

FOREIGN PATENT DOCUMENTS

JP 11-337656 A 12/1999
JP 2008-002973 A 1/2008
(Continued)

OTHER PUBLICATIONS

Barac et al., "Advances in Eddy Current Measurement of Residual Stress", *The 7th International Conference on Shot Peening*, Jan. 1, 1999, pp. 326-335.
(Continued)

*Primary Examiner* — Bot Ledynh
(74) *Attorney, Agent, or Firm* — Brinks Gilson & Lione

(57) ABSTRACT

To provide a surface property inspection apparatus, surface property inspection system, and surface property inspection method capable of inspecting the surface processing state of processed material subjected to surface processing such as shot-peening, heat treatment, or nitriding with high accuracy and low vulnerability to temperature changes in the inspection environment. Surface property inspection apparatus is furnished with a AC power supply, a AC bridge circuit, and an evaluation device; AC bridge circuit comprises variable resistor with which distribution ratio γ is variable, reference detector, and inspection detector. Inspection detector is furnished with a coil wound so as to oppose the surface property inspection region of object under inspection M, and by supplying AC power from AC power supply to coil, an eddy current is excited in object under inspection M. Thus the magnetic properties of object under inspection M can be detected, and inspection of surface properties based on the output signal from AC power supply is possible.

19 Claims, 21 Drawing Sheets

(51) Int. Cl.
*G01N 27/80* (2006.01)
*G01R 33/12* (2006.01)
*G01N 27/90* (2006.01)
*C21D 7/06* (2006.01)
*C21D 11/00* (2006.01)

(58) Field of Classification Search
USPC .................................................. 324/240, 243
See application file for complete search history.

(56) References Cited

U.S. PATENT DOCUMENTS

| | | | |
|---|---|---|---|
| 7,567,873 B2 | 7/2009 | Kojima et al. | |
| 8,884,615 B2* | 11/2014 | Gati et al. | 324/252 |
| 9,056,386 B2 | 6/2015 | Kobayashi | |
| 2005/0017712 A1* | 1/2005 | Le | 324/230 |
| 2008/0001609 A1 | 1/2008 | Kojima et al. | |
| 2009/0013777 A1* | 1/2009 | Ohtsuka et al. | 73/204.15 |
| 2009/0278532 A1* | 11/2009 | Pettigrew | 324/207.21 |
| 2011/0121828 A1* | 5/2011 | Gati et al. | 324/252 |
| 2012/0180539 A1 | 7/2012 | Kobayashi | |
| 2014/0084910 A1 | 3/2014 | Makino | |

FOREIGN PATENT DOCUMENTS

| | | |
|---|---|---|
| JP | 2009-236762 A | 10/2009 |
| JP | 2010-230350 A | 10/2010 |
| JP | 2013-053984 A | 3/2013 |
| JP | 2013-529286 A | 7/2013 |
| WO | WO 2011/040243 A1 | 4/2011 |
| WO | WO 2012/153862 | 11/2012 |

OTHER PUBLICATIONS

Chang et al., "Non-Destructive Residual Stress Measurement Using Eddy Current", *International Conference on Shot-Peening*, Jan. 1, 1996, pp. 356-384.
International Search Report for PCT/JP2014/054100 dated May 14, 2014, 3 pages.
Eddy Current Testing I, "Non-destructive testing technique series," and partial English language translation thereof, Apr. 20, 2008, Third Printing, ISBN 978-4-931018-11-2, pp. 32-38, 13 pages.

* cited by examiner

SURFACE PROPERTY INSPECTION APPARATUS, SURFACE PROPERTY INSPECTION SYSTEM, AND SURFACE PROPERTY INSPECTION METHOD

RELATED APPLICATIONS

This application is a continuation application of PCT/JP2014/054100 having an international filing date of Feb. 14, 2014, which claims priority to JP 2013-113694 filed May 30, 2013, the entire contents of which are incorporated herein by reference.

TECHNICAL FIELD

The present invention pertains to a surface property inspection apparatus for non-destructive inspection of the surface processing state of processed material subjected to surface processing such as shot-peening, heat treatment, or nitriding.

BACKGROUND ART

Surface processing such as surface hardening or shot-peening by heat treatment, nitriding, and the like is applied to steel parts such as gears and shafts used as automobile parts, etc. to improve friction resistance, fatigue strength, and the like.

Conventionally, evaluation of surface properties such as residual stress and hardness after surface processing of such products has been performed by sample destructive inspection. This resulted in the problem that not all products could be directly inspected, and inspected products became unusable, since inspection was destructive.

This has led to a strong requirement to develop a device capable of non-destructively inspecting product surface properties. As an example of such a device, Patent Document 1 discloses a non-destructive inspection apparatus for a shot-peened surface, wherein an AC signal is input while varying the frequency to an inspection circuit furnished with a coil disposed above a shot-peened surface, and the state of generation of residual stress in the inspected object is inspected using the impedance frequency response characteristics of the inspection circuit.

PRIOR ART REFERENCES

Patent References

Patent Document 1: Unexamined Patent Application Publication 2008-2973

However, because elements of electromagnetic measurements of properties such as magnetic permeability or conductivity, which vary with surface processing, are affected by environmental changes, the problem arises in the device set forth in Unexamined Patent Application Publication 2008-2973 that measurement errors can easily occur when the environment for measuring a reference test piece differs from the environment for measuring objects under inspection, especially when temperature variations occur. This makes it difficult to adopt the device for in-line measurements. Also, because this is a localized measurement, heat-generating effects caused by the concentration of eddy currents can easily occur, and a huge amount of time is required if attempting to inspect the entire surface-processed portion. Moreover, when using a contacting detectors, shape-matched detectors must be prepared for each object under inspection, so that this is not a device with high general applicability.

The present invention therefore has the object of providing a surface property inspection apparatus, surface property inspection system, and surface property inspection method capable of inspecting the surface processing state of processed material subjected to surface processing such as shot-peening, heat treatment, or nitriding with high accuracy and low susceptibility to temperature changes in the inspection environment.

SUMMARY OF THE INVENTION

To achieve the foregoing object, the invention of claim 1 uses a technical means, being a surface property inspection apparatus for inspecting surface properties of an object under inspection subjected to surface processing, comprising: an AC bridge circuit; an AC power supply for supplying AC power to the AC bridge circuit; and an evaluation apparatus for evaluating the surface properties of the object under inspection based on an output signal from the AC bridge circuit; wherein the AC bridge circuit has a variable resistor configured so that the distribution ratio is variable between a first resistor and a second resistor, an inspection detector furnished with a coil for creating an AC magnetic field and exciting an eddy current in the object under inspection, and a reference detector for inspecting a reference state serving as reference for comparing with the output from the inspection detector; and whereby the first resistor, the second resistor, the reference detector, and the inspection detector constitute the AC bridge circuit; and wherein the evaluation apparatus evaluates the surface properties of the object under inspection based on an output signal from the AC bridge circuit, in a state whereby AC power is supplied to the AC bridge circuit, the inspection detector detects an electromagnetic properties of the object under inspection and the reference detector detects a reference state.

The invention of claim 1 is capable of exciting an eddy current in an object under inspection using an inspection detector coil, and of evaluating surface properties of the object under inspection based on an output signal from an AC bridge circuit. This enables high precision inspection of the surface state with a simple circuit configuration. Since a method is adopted in which surface properties of the object under inspection are inspected by exciting an eddy current, the effects of temperature variations in the inspection environment can be reduced. The term "surface property" here refers to "properties from the outermost surface down to the internal influencing layer of the object under inspection."

In the Claim 2 invention, the coil in the Claim 1 surface property inspection device is wound to surround a surface property inspection region of the object under inspection, and an eddy current is excited in the surface property inspection region by supplying AC power to the coil.

Using the invention of Claim 2, magnetism can be stably supplied to the object under inspection, and the surface property inspection region of the object under inspection can be inspected in one pass. Also, because the eddy current can be diffused and the emission of heat in the surface of the object under inspection suppressed, thermal changes in the object under inspection can be minimized, thereby enabling more accurate inspection.

In the Claim 3 invention, the surface property inspection apparatus uses a technical means whereby in the surface property inspection apparatus of Claim 2, the surface property inspection apparatus is built into a surface treatment apparatus for performing shot-peening as the surface processing, furnished with a moving mechanism for positioning the object under inspection at an evaluation position, which is the inside of the coil of the inspection detector, by transporting and moving the object under inspection or the inspection detector.

In the Claim 3 invention the surface property inspection apparatus is furnished with a moving mechanism built into a surface treatment apparatus for performing shot-peening as a surface processing, thereby enabling rapid inspection of an object under inspection after shot-peening. Since a detection device can be packaged with the surface property inspection apparatus (shot-peening apparatus) and provided to customers, the value of the surface treatment apparatus (shot-peening apparatus) can be increased, as can customer satisfaction.

The Claim 4 invention is the surface property inspection apparatus of Claim 2, further comprising a first transport mechanism, whereby the object under inspection is drivable up or down, and the object under inspection is transported to an evaluation position inside the inspection detector coil and to a position either above or below said evaluation position, or both; and a registration portion for registering the object under inspection at a position within a horizontal plane; whereby surface properties of the object under inspection are evaluated either in-line or out-line in a surface processing step by a shot-peening apparatus for performing shot-peening as surface processing.

In the Claim 4 invention, a registration portion and a first transport mechanism for registering an object under inspection are provided, thereby enabling the object under inspection to be positioned at an appropriate position when evaluating surface properties, such that a high accuracy, reliable inspection can be performed. This registration portion and first transport mechanism allow for automation and enable in-line inspection. Here "in-line" inspection means automatically performed inspection in which transport of the object under inspection before and after shot-peening (loading and unloading of objects under inspection to and from the shot-peening apparatus, and loading and unloading to and from the evaluation position) is performed by a robot or the like, and refers to inspection matched to the production rate of the shot-peening line. "Out-line" inspection means inspection in which the transporting of the object under inspection before and after shot-peening is performed by hand, and is not matched to the production rate of the shot-peening line.

Inspection in which there is no requirement to dispose an inspection apparatus before the shot-peening apparatus and inspection is performed in a location outside the line is also out-line inspection.

In the Claim 5 invention, a technical means is used whereby the inspection detector in the surface property inspection apparatus of Claim 3 or 4 is configured to excite an eddy current in an object under inspection furnished with a gear portion.

For example, a member furnished with a gear portion such as a gear is difficult to inspect in its entirety with a contacting detector, but can be easily inspected using the surface property inspection apparatus of the present invention.

In the Claim 6 invention, a technical means is used whereby in the Claim 5 surface property inspection apparatus, the inspection detector is further furnished with a magnetic shield disposed on the outside of the coil to surround the object under inspection, blocking off external magnetism.

In the Claim 6 invention, because external magnetism is blocked, detection sensitivity to electromagnetic properties can be improved, and detection sensitivity to electromagnetic properties corresponding to surface processing state can be improved, therefore the surface processing state of the object under inspection can be more accurately evaluated.

In the Claim 7 invention, a technical means is used whereby in the Claim 6 surface property inspection apparatus, a temperature sensor is further provided for measuring the temperature of the surface of the object under inspection; the evaluation apparatus makes a pass/fail judgment of the surface processing state of the object under inspection if the temperature detected by the temperature sensor is within a predetermined range, and does not make a pass/fail judgment of the surface processing state of the object under inspection if the temperature detected by the temperature sensor is outside a predetermined range.

In the Claim 7 invention, a pass/fail judgment of the surface processing state of the object under inspection can be omitted when the temperature detected by the temperature sensor affects the accuracy of the inspection, thereby permitting a high accuracy inspection to be performed.

The Claim 8 invention is a surface processing apparatus, comprising the surface property inspection apparatus of Claim 3, and a holding portion for holding the object under inspection in a registered state, the surface processing apparatus performing shot-peening as surface processing, wherein the object under inspection held by the holding portion is positioned at an evaluation position inside the coil of the inspection detector by transporting and moving the object under inspection held by the holding portion or the inspection detector, and the surface property inspection apparatus inspects the surface properties of the object under inspection before and after shot-peening or after shot-peening.

In the Claim 8 invention, a holding portion is provided for holding the object under inspection in its registered state, thereby enabling the object under inspection to be positioned at an appropriate position when evaluating surface properties so that a high accuracy inspection can be performed. This holding portion enables automation and in-line inspection. Since a detection device can be packaged with the surface property inspection apparatus (shot-peening apparatus) and provided to customers, the value of the surface treatment apparatus (shot-peening apparatus) can be increased, as can customer satisfaction.

The Claim 9 invention uses a technical means which is a surface processing system furnished with the Claim 4 surface property inspection apparatus, a surface processing apparatus for performing shot-peening as the surface processing, a second transport mechanism for transporting the object under inspection moved to a first standby position by the first transport mechanism in a horizontal direction or a direction inclined relative to the horizontal direction, and for transporting the object under inspection up to a predetermined position on the surface processing apparatus, and a third transport mechanism capable of transporting the object under inspection in a horizontal direction or a direction inclined relative to the horizontal direction, and of transporting the object under inspection from a pre-shot-peening area via a second standby position to a shot-peening and inspection-completed area; whereby the first standby position is a position above or below the evaluation position and facing the surface processing position, the second standby position is the evaluation position or a position above or below the evaluation position, the third transport mechanism transports the object under inspection from the pre-shot-peening area up to the second standby position and by movement of at least one of either the object under inspection or the inspection detector transported to the second standby position, the object under inspection is positioned in the evaluation position of the inspection detector, and the third transport mechanism transports an object under inspection moved to the second standby position by the first transport mechanism to the shot-peening and inspection-completed area.

In the Claim 9 invention, a first transport mechanism and a registration portion are provided, therefore this registration portion can position the object under inspection at an appropriate position when evaluating surface properties, such that a high accuracy, reliable inspection can be performed. The combination of a first transport mechanism, second conveyor mechanism, and third transport mechanism allows for in-line inspection. The first transport mechanism and the registration portion can implement the above-described proper inspection and transport the object under inspection in an appropriate state to the second transport mechanism, and implement transport by the second transport mechanism to an appropriate position on the surface property inspection apparatus. I.e., registration on the surface property inspection apparatus is achieved with a simple structure.

The Claim 10 invention uses a technical means whereby the Claim 9 surface processing system is further furnished with an inspection detector transport mechanism for moving the inspection detector up and down, and the second standby position is the evaluation position; when the object under inspection is transported as far as the second standby position, the object under inspection is positioned at the evaluation position of the inspection detector by the movement of the inspection detector up or down by the inspection detector transport mechanism.

As in the Claim 10 invention, a configuration can be adopted whereby the object under inspection is positioned at the inspection detector evaluation position by moving the inspection detector up or down using the inspection detector transport mechanism.

The Claim 11 invention uses a technical means whereby in the Claim 9 surface processing system, the second standby position is a position either above or below the evaluation position, and an object under inspection transported as far as the second standby position is positioned at the evaluation position of the inspection detector by being moved up or down by the first transport mechanism.

In the Claim 11 invention it is possible to perform an inspection by moving only the object under inspection, with the inspection detector position fixed, making it unnecessary to provide an inspection detector transport mechanism, and reducing the likelihood of positioning error.

The Claim 12 invention uses a technical means which is a surface property inspection method in which a surface property inspection apparatus according to any of Claims 1 through 4 is prepared, furnished with a disposition step for disposing the inspection detector so that an eddy current is excited in the object under inspection with AC power supplied to the AC bridge circuit, and an evaluation step for evaluating the surface properties of the object under inspection based on an output signal output from the AC bridge circuit.

In the Claim 12 invention, using a surface property inspection apparatus an inspection detector is disposed in a disposition step so that an eddy current is excited in an object under inspection by AC power supplied from an AC power supply to an AC bridge circuit, so that surface properties of the object under inspection can be evaluated in an evaluation step based on an output signal output from the AC bridge circuit.

With the Claim 13 invention, a technical means is used whereby in the Claim 12 surface property inspection method, a reference test object is prepared and measured in order to output a reference output for detecting a reference state in the reference detector.

Using the Claim 13 invention, a reference test object is used to output a reference output in order to detect a reference state in a reference detector, therefore by using a reference test object with a known good surface processing state, pass/fail of the surface state of an object under inspection can be evaluated by comparison with the reference test object.

With the Claim 14 invention, a technical means is used whereby in the Claim 12 surface property inspection method, a reference inspection piece is not used in order to output a reference output for detecting a reference state in the reference detector.

Using the Claim 14 invention, a reference test object is not used to output a reference output in order to detect a reference state in a reference detector, therefore a high accuracy inspection is possible without being affected by temperature changes in the reference test object.

In the Claim 15 invention, a technical means is used whereby in the Claim 14 surface property inspection method, the surface properties of the object under inspection are respectively measured before and after surface processing, and a pass/fail judgment of the surface processing state of the object under inspection is made by comparing the respective measured values.

In the Claim 15 invention, changes in surface properties can be found by comparing surface properties before and after surface processing, therefore a more accurate and precise inspection can be performed.

The Claim 16 invention uses a technical means whereby the reference detector in the Claim 1 surface property inspection apparatus has a coil and a ferromagnetic core disposed on the inside of this coil, in which an eddy current is excited by supplying AC power to the coil.

Using the Claim 16 invention, the reference detector is furnished with a coil; a ferromagnetic core is disposed inside this coil rather than a reference test object, therefore the reference detector can be constituted without reliance on the dimensions and shape of the object under inspection, thus enabling the size of the reference detector to be reduced.

The Claim 17 invention uses a technical means whereby in the claim 16 surface property inspection apparatus the AC bridge circuit is furnished with a printed circuit board, and a variable resistor and the reference detector are disposed on this printed circuit board.

In the Claim 17 invention a variable resistor and reference detector are disposed on a printed circuit board such that there is no need to separately handle the reference detector, thereby permitting easier handling of the surface property inspection apparatus and an improved degree of freedom for installing the surface property inspection apparatus.

DETAILED DESCRIPTION OF THE PREFERRED EMBODIMENTS

Surface Property Inspection Apparatus

Figure 1A:
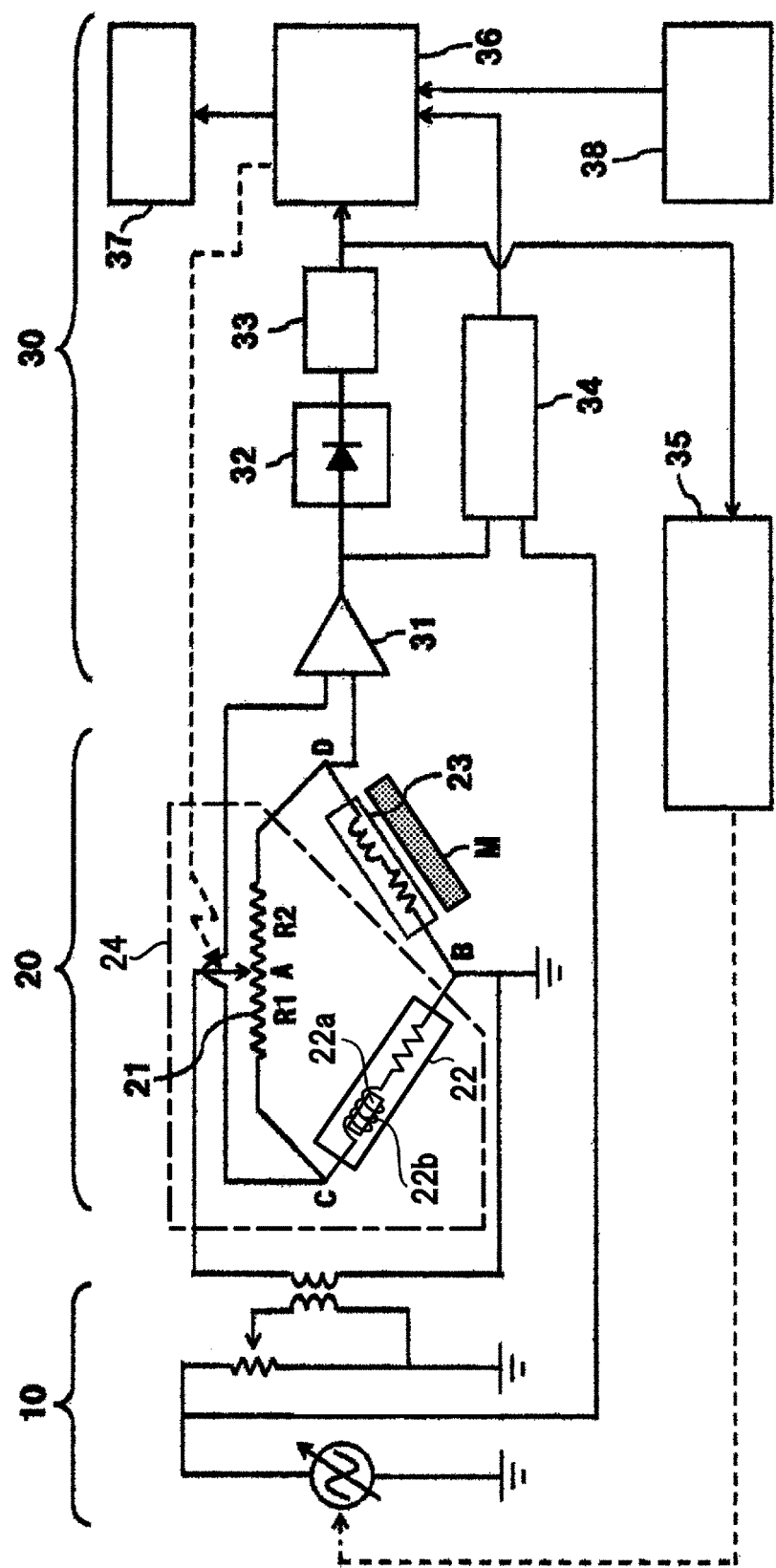
FIG. 1A is a diagram depicting the constitution of a surface property inspection apparatus, showing the circuit configuration of a surface property inspection apparatus.

As shown in FIG. 1A, surface property inspection apparatus 1 according to an embodiment of the present invention is furnished with an AC power supply 10, an AC bridge circuit 20, and an evaluation device 30.

AC power supply 10 is capable of supplying AC power at a variable frequency to AC bridge circuit 20.

AC bridge circuit 20 is furnished with a variable resistor 21, a reference detector 22, an inspection detector 23 formed to permit disposition of a coil to excite an eddy current in object under inspection M, and a reference detector 22 for detecting a reference state serving as reference for comparison with the output from inspection detector 23.

A variable resistor 21 is constituted to variably distribute the distribution ratio γ of a resistor $R_A$ into resistor R1 and resistor R2. Resistor R1 and resistor R2, together with reference detector 22 and inspection detector 23, constitute a bridge circuit. In the present embodiment, point A dividing between resistor R1 and resistor R2, and point B between reference detector 22 and inspection detector 23, are connected to the AC power supply 10 of evaluation device 30, and point C between resistor R1 and reference detector 22, and point D between resistor R2 and inspection detector 23, are connected to amplifier 31. To reduce noise, the reference detector 22 and inspection detector 23 side is grounded.

Evaluation device 30 is furnished with an amplifier 31 for amplifying a voltage signal output from AC bridge circuit 20, an absolute value circuit 32, a low-pass filter (LPF) 33, a phase comparator 34 for comparing the phases between the AC voltage supplied from AC power supply 10 and the voltage output from amplifier 31, a frequency adjuster 35 for adjusting the frequency of the AC voltage supplied from AC power supply 10, a judgment means for performing a non-equilibrium adjustment to optimize the distribution between R1 and R2 and judge a pass/fail state of the surface of object under inspection M based on the output from LPF 33, a display means 37 for displaying and warning the judgment results by judgment means 36, and a temperature sensor 38 for detecting the temperature at the evaluation position.

Amplifier 31 is connected to points C and D and receives an input of the potential difference between point C and point D. Absolute value circuit 32 and LPF 33 are connected, in that order, to judgment means 36. Phase comparator 34 is compared to AC power supply 10, amplifier 31, and judgment means 36. Frequency adjuster 35 is connected to AC power supply 10 and amplifier 31. Judgment means 36, by outputting a control signal, can change the position of point A in AC bridge circuit 20, i.e. can change the distribution ratio γ between resistor R1 and resistor R2; the variable resistance setting step described below is in this way executed.

Temperature sensor 38 comprises a non-contacting infrared sensor or thermocouple, and outputs a temperature signal for the surface of the object under inspection M to judgment means 36. When the temperature of object under inspection M detected by temperature sensor 38 is within a predetermined range, judgment means 36 makes a pass/fail judgment of the surface processing state of object under inspection M; when the temperature detected by temperature sensor 38 is outside a predetermined range, pass/fail judgment is not made of the surface processing state of object under inspection M. This enables the pass/fail judgment of the surface processing state of object under inspection M to be omitted when the temperature detected by the temperature sensor affects the accuracy of the inspection, thereby permitting a high accuracy inspection to be performed. Here, a configuration may be adopted in which the temperature of evaluation position Ts is measured using a thermocouple or the like, and a judgment is made of the pass/fail state of the surface processing of object under inspection M using the surface temperature of object under inspection M as a representative temperature.

As an inspection detector 23 and reference detector 22 of the same constitution as inspection detector 23, a coil is wound and formed around a core which is insertable into the evaluation portion of the object under inspection; the detector used has a coil which can be opposed to the surface of object under inspection M and brought into proximity thereto to excite an eddy current in object under inspection M. In other words, this coil is wound so as to surround and oppose the surface property inspection region of the object under inspection. "Surround the surface property inspection region of the object under inspection" here includes the meaning of exciting an eddy current in the surface property inspection region by enveloping (surrounding so as to wrap) at least a portion of the surface property inspection region.

Figure 1B:
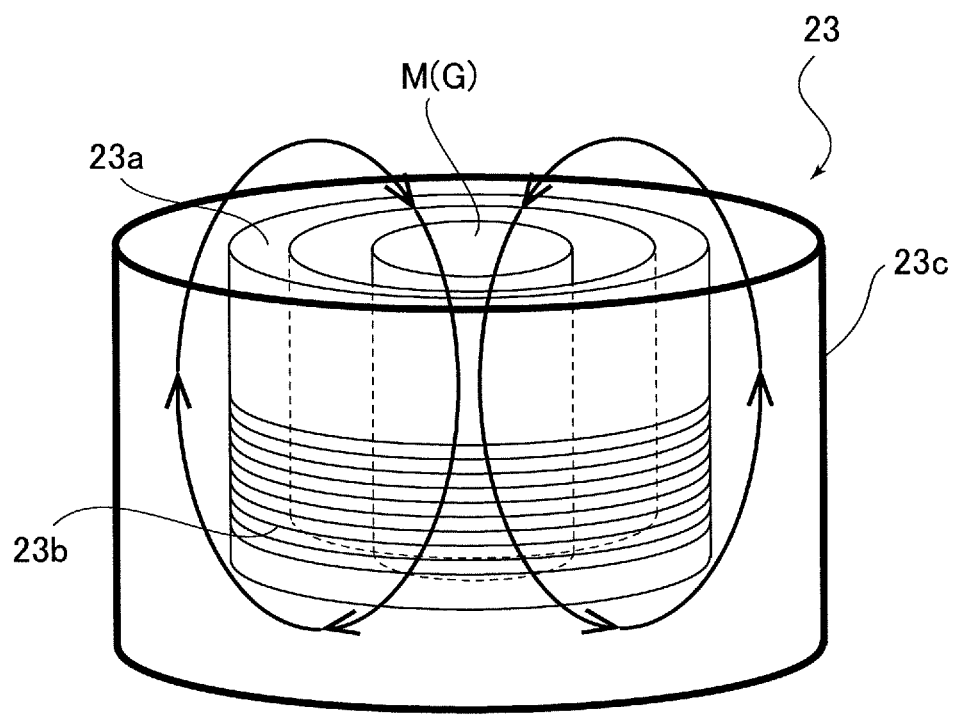
FIG. 1B is an explanatory diagram showing the constitution of a surface property inspection apparatus, being a transparent diagram depicting the constitution of an inspection detector.

Here we discuss an object under inspection furnished with a gear portion as object under inspection M, e.g., an inspection detector 23 used to inspect the surface properties of a gear G in which the gear portion has been surface processed. inspection detector 23, as shown in FIG. 1B, is furnished with a cylindrical core 23a formed to cover the gear portion of gear G, and a coil 23b wound around the outer perimeter surface of core 23a. Core 23a is formed of a non-magnetic material such as resin. Note that the shape of core 23a is not limited to a cylinder so long as it can be disposed inside gear G. Note also that reference test piece S for outputting a reference output may be disposed, without disposing an object under inspection M.

Inspection detector 23 has the feature that it captures eddy current reactions with high accuracy when evaluating surface properties, therefore it should preferably be disposed relative to object under inspection M so that eddy currents flow in the region in which one wishes to inspect surface properties. I.e., it is preferable that the direction of windings in coil 23b be disposed in the same direction as the direction in which one wishes to source eddy currents.

Shot-peening of gear G causes a residual stress layer to form in the gear portion. When evaluating gear G as the object under inspection M, it is preferable to evaluate the surface properties of not only the tooth tip, but also the tooth surface and tooth bottom. To do this, the winding direction of coil 23b is disposed essentially perpendicular to the rotational axis of gear G. Since a magnetic loop is generated in the rotational direction, this enables an eddy current to be excited in the rotational direction of gear G, such that not only the tooth tip, but also the tooth surface and tooth bottom can be evaluated. Conventional contacting detectors required multiple types of detector to be prepared to fit the shape of the tooth being inspected, and surface properties close to the contacting portion could not be inspected, but with inspection detector 23 a broad range of surface properties can be inspected at once with a single detector.

Inspection detector 23 does not have to be furnished with a core 23a so long as coil 23b can maintain a shape. Such a coil 23b may be formed, for example, by adhesion of an enamel copper wire in an air core using a hardening epoxy resin or the like, or by winding around an air core using a heat-hardening fusing enamel copper wire, then hardening with heat from hot air or a drying oven.

Inspection detector 23 is disposed so that coil 23b opposes and surrounds the surface to be inspected of object under inspection M; an AC magnetic field is generated when AC power at a predetermined frequency is supplied to coil 23b by AC power supply 10, and an eddy current flowing in a direction crossing the AC magnetic field is excited on the surface of object under inspection M. Since eddy currents change in response to electromagnetic properties of the residual stress layer, the phase and amplitude (impedance) of the output waveform output from amplifier 31 changes in response to properties of the residual stress layer (the surface processing state). Electromagnetic properties of the surface processing layer can be detected using these changes in output waveform to perform an inspection.

I.e., by supplying AC power to coil 23b, an AC magnetic field is generated in a direction parallel to the axis of coil 23b inside coil 23b. This AC magnetic field is disposed inside coil 23b, and on coil 23b inside non-contacting gear G, an eddy current is excited in a direction perpendicular to the direction of the AC magnetic field. An eddy current is thus excited inside gear G, in the rotational direction of gear G. Since a large amount of eddy current thus flows in the surface property inspection region of the gear G (close to the outer perimeter surface of gear G) for which surface properties are to be inspected, the surface processing state of the surface property inspection region is strongly reflected in the excited eddy current. Thus by disposing the object under inspection so that an AC magnetic field is generated approximately parallel to the surface for which surface properties are to be inspected (the surface property inspection region), surface properties can be detected with good sensitivity. Stated another way, it is desirable to dispose the surface property inspection region in a direction along the inner perimeter surface of the coil.

Eddy current excited inside gear G is distributed essentially uniformly in the surface property inspection region (close to the outer perimeter surface of gear G), therefore properties of the entire surface property inspection region are reflected in the eddy current, and the surface processing state of the entire surface property inspection region can be accurately detected. In addition, because eddy currents are distributed over the entire surface property inspection region, degradation of detection accuracy due to temperature increases in the object under inspection caused by the flow of large localized eddy currents can be prevented.

Furthermore, because the gear G, which is the workpiece, is surrounded, and a greater amount of change in eddy current can be captured, the effects of temperature changes in the inspection environment can be reduced.

It is also possible to provide a magnetic shield 23c, disposed outside inspection detector 23 and surrounding object under inspection M. By using magnetic shield 23c, external magnetism is blocked, therefore detection sensitivity to electromagnetic properties can be improved, and detection sensitivity to electromagnetic properties corresponding to surface processing state can be improved, and the surface processing state of object under inspection M can be more accurately evaluated.

Output from the AC Bridge Circuit

Figure 2:
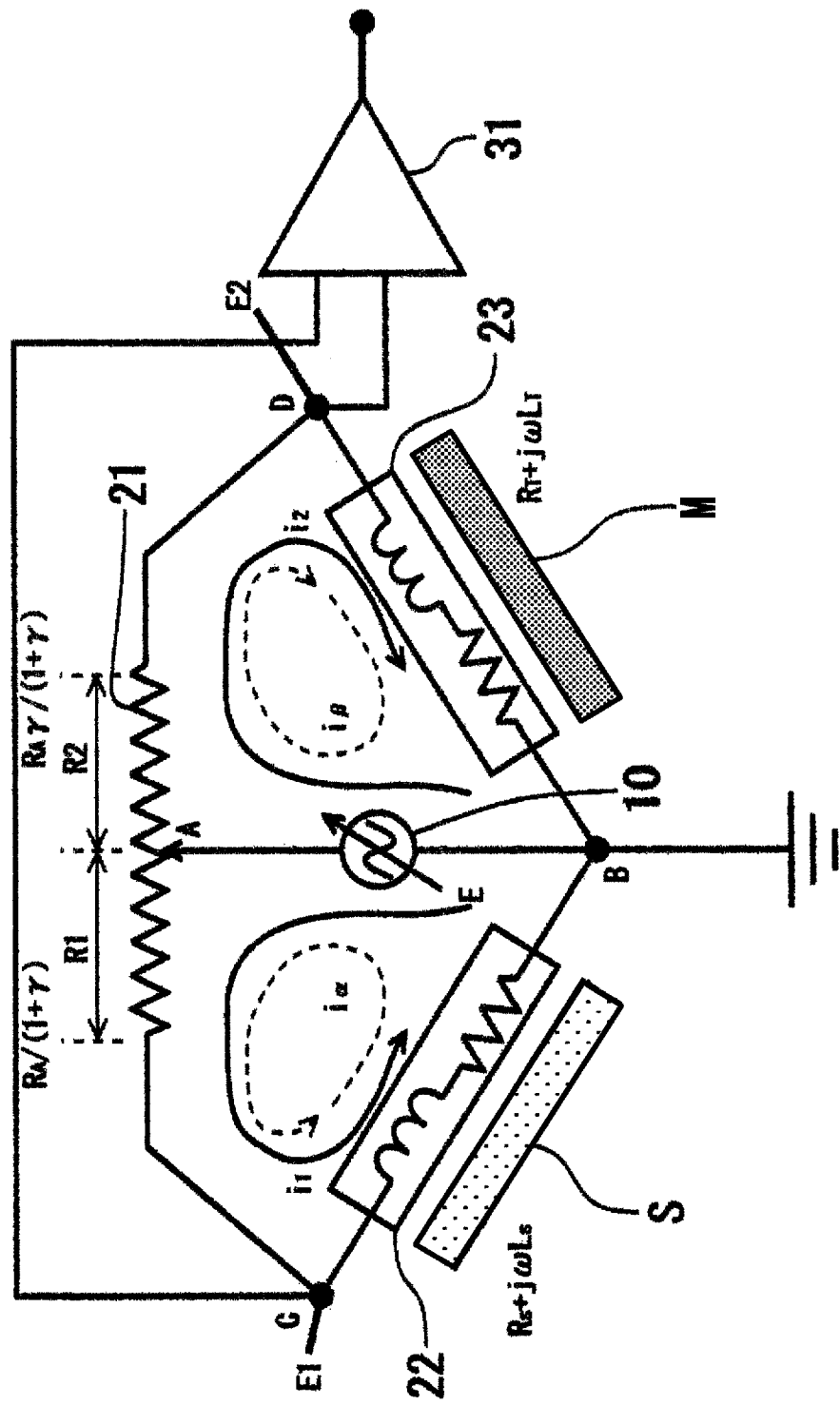
FIG. 2 is an equivalent circuit diagram explaining the output from an AC bridge circuit.

Next, referring to the equivalent circuit in FIG. 2, we explain the output from AC bridge circuit 20, adjusted to a non-equilibrium state. A reference test piece S with a guaranteed good surface processing state is for example brought into proximity with reference detector 22 in order to output a reference output, and an object under inspection M for pass/fail determination of the surface processing state is brought into proximity with inspection detector 23. Note that, as discussed below, it is also possible not to bring reference test piece S into proximity with reference detector 22, i.e. to inspect surface properties without using reference test piece S. Below we discuss a case in which reference test piece S is used, but except for the fact that the below-described $i\alpha$ reaches 0, the same statements apply when reference test piece S is not used, so an explanation thereof is here omitted. Note that in the surface property inspection method described below we explain the case in which reference test piece S is not used.

With a distribution of $\gamma$ for variable resistor $R_A$, resistor R1 equals $R_A/(1+\gamma)$, and resistor R2 equals $R_A \gamma/(1+\gamma)$. The impedance of reference detector 22 is referred to as $R_S+jwL_S$, and the impedance of inspection detector 23 is referred to as $R_T jwL_T$. The potential at point A is referred to as E; excitation current flowing on each side of the bridge when the objects under inspection (reference test piece S, object under inspection M) are not brought into proximity with reference detector 22 and inspection detector 23 are respectively $i_1$ and $i_2$; the amount of excitation changes as the objects under inspection are brought into proximity with reference detector 22 and inspection detector 23, and the currents flowing in response to that change amount are respectively referred to as $i\alpha$ and $i\beta$. The potentials E1 and E2 and the excitation currents $i_1$ and $i_2$ of reference detector 22 and inspection detector 23 at this time are shown by Equations (1) through (4) below.

$$E1 = (R_S + j\omega L_S)(i\alpha + i_1) \quad (1)$$

$$E2 = (R_T + j\omega L_T)(i\beta + i_2) \quad (2)$$

$$i_1 = \frac{E}{\frac{R_A}{1+\gamma} + R_S + j\omega L_S} \quad (3)$$

$$i_2 = \frac{E}{\frac{R_A \gamma}{1+\gamma} + R_T + j\omega L_T} \quad (4)$$

The voltage output to amplifier 31 is the differential between E1 and E2, and is expressed by the following equation:

$$E2-E1=[\{(R_T j\omega L_T)i\beta-(R_S j\omega L_S)i\alpha\}+\{(R_T+j\omega L_T)i_2-(R_S+j\omega L_S)i_1\}] \quad (5)$$

The following equation is derived from Eqs. (3) through (5).

$$E2 - E1 = \left[\begin{array}{c} \{(R_T + j\omega L_T)i\beta - (R_S + j\omega L_S)i\alpha\} + \\ \left\{\begin{array}{c} (R_T + j\omega L_T)\dfrac{E}{\dfrac{R_A}{1+\gamma} + R_S + j\omega L_T} - \\ (R_S + j\omega L_S)\dfrac{E}{\dfrac{R_A}{1+\gamma} + R_S + j\omega L_S} \end{array}\right\} \end{array}\right] \quad (6)$$

We will divide the right side of Eq. (6) into components A and B and consider each of the components of the differential voltage.

Component A:

$$(R_T+j\omega L_T)i\beta-(R_S+j\omega L_S)i\alpha$$

Component B:

$$(R_T + j\omega L_T)\frac{E}{\frac{R_A \gamma}{1+\gamma} + R_T + j\omega L_T} - (R_S + j\omega L_S)\frac{E}{\frac{R_A}{1+\gamma} + R_S + j\omega L_S}$$

Component A comprises each of the detector components: $(R_S+jwL_S)$ and $(R_T+jwL_T)$, and the current flow amount which changes when each of the test objects is brought into proximity with each detector are $i\alpha$ and $i\beta$. The size of $i\alpha$ and $i\beta$ varies with the amount of magnetism passing through the test object due to electromagnetic properties such as magnetic permeability and electrical conductivity. For this reason, the size of $i\alpha$ and $i\beta$ can be changed by changing the excitation currents $i_1$, $i_2$ which control the amount of magnetism generated by each detector. According to Eqs. (3) and (4), excitation currents $i_1$, $i_2$ change according to the variable resistor distribution ratio $\gamma$, therefore the size of component A can be changed by adjusting variable resistor distribution ratio $\gamma$.

Component B comprises each of the detector components: $(R_S+jwL_S)$, $(R_T+jwL_T)$, and the resistance parameter divided by variable resistor distribution ratio $\gamma$. Therefore the size of component B can be changed by adjusting variable resistor distribution ratio $\gamma$ in the same way as component A.

When object under inspection M is disposed at a predetermined position and AC power at a predetermined frequency is supplied to inspection detector 23 coil 23b by AC power supply 10, an eddy current flowing in a direction crossing the AC magnetic field is excited on the surface of object under inspection M. Since eddy currents change in response to electromagnetic properties of the residual stress layer, the phase and amplitude (impedance) of the output waveform output from amplifier 31 changes in response to properties of the residual stress layer (the surface processing state). Electromagnetic properties of the residual stress layer can be detected using these changes in output waveform to perform an inspection of the surface processing layer.

Signals output from bridge amplifier 31 are signals which extract the differential surface area between the voltage waveforms of reference detector 22 and inspection detector 23; the circuit structure is one in which the current flowing in the detector (excitation current) is held steady, therefore the extracted voltage signals can be thought of as a power signal. Power supplied to the detector is always constant, and the magnetic energy supplied to object under inspection M can also be held steady.

Surface Property Inspection Method

Figure 3:
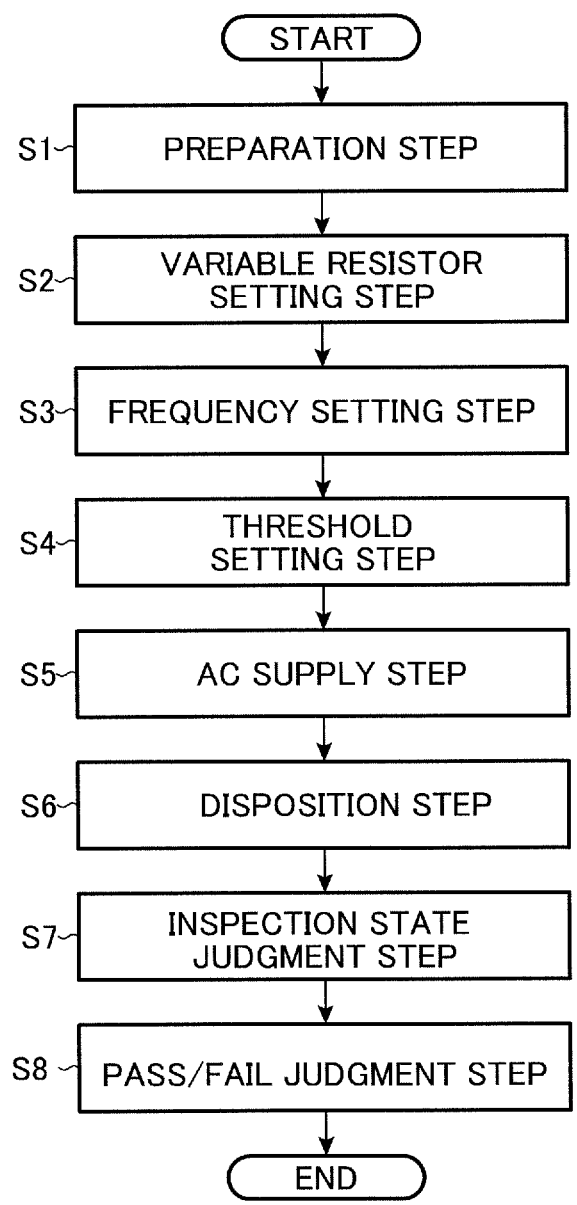
FIG. 3 is a flow chart showing a surface property inspection method.

Next, referring to FIG. 3, we explain a method for inspecting the surface properties of an object under inspection using surface property inspection apparatus 1.

First, in preparatory step S1, surface property inspection apparatus 1 and a reference test piece S with known good surface processing are prepared. It is also acceptable to prepare an object under inspection on which no surface processing is performed, or a reference test piece on which the surface processing state is poor.

Next a variable resistor setting step S2 is performed. In variable resistor setting step S2, AC power is first supplied from AC power supply 10 to AC bridge circuit 20. In this state, the distribution ratio $\gamma$ of variable resistor 21 is set to raise the detection sensitivity of surface property inspection apparatus 1 relative to the object under inspection. I.e., the distribution ratio γ of variable resistor 21 is adjusted so that the output signal of AC bridge circuit 20 is reduced without bringing the object under inspection into proximity with inspection detector 23. By thus setting variable resistor 21, the difference is increased between the case when the surface processing state of an object under inspection M brought into proximity with inspection detector 23 and is bad vs. the case when the surface processing is known good, thereby enabling detection accuracy to be raised. Specifically, using a display device with a waveform display function such as an oscilloscope (such as that with which judgment means 36 is provided), the voltage amplitude of the output signal from AC bridge circuit 20 or the voltage output from LPF 33 are monitored, and distribution ratio γ is adjusted to reduce the output. The distribution ratio γ of variable resistor 21 is preferably adjusted and set so that the output reaches a minimum value or a local minimum value (local equilibrium point).

Adjustment of variable resistor 21 distribution ratio γ is performed to increase the output difference in response to the difference in surface states by reducing differential voltage (E2−E1), thereby raising detection accuracy. As described above, components A and B are changed by adjusting distribution ratio γ, therefore variable resistor 21 distribution ratio γ can be adjusted in response to the impedance $(R_S+jwL_S)$ and $(R_T+jwL_T)$ of reference detector 22 and inspection detector 23, and the differential voltage (E2−E1), which is the output from AC bridge circuit 20, can be reduced. Thus the difference in properties between reference detector 22 and inspection detector 23 can be reduced and at least a little more of the inherent properties of object under inspection M can be extracted, thereby improving detection accuracy.

In frequency setting step S3, AC power is supplied from AC power supply 10 to AC bridge circuit 20 with reference test piece S brought into proximity with inspection detector 23, the frequency of AC power supplied to AC bridge circuit 20 by frequency adjuster 35 is varied, and the voltage amplitude output from AC bridge circuit 20 or the voltage output from LPF 33 are monitored.

Frequency adjuster 35 outputs a control signal to AC power supply 10 to achieve the initial frequency f1 set in frequency adjuster 35, and the output voltage Ef1 from amplifier 31 at frequency f1 is input to frequency adjuster 35 and stored. Next, a control signal is output to AC power supply 10 so as to reach a frequency f2 which is higher than frequency f1 by a predetermined value, such as 100 Hz; an output voltage Eft from amplifier 31 at frequency 12 is input to frequency adjuster 35 and stored.

Next, a comparison is made between Ef1 and Ef2; if Ef2>Ef1, a control signal is output so as to reach a frequency f3 higher by a predetermined value than frequency 12; an output voltage Ef3 from amplifier 31 at frequency 13 is input to frequency adjuster 35 and stored. A comparison is then made between Ef2 and Ef3. This is repeated, and the frequency fn when Efn+1<Efn, i.e. the frequency fn at which output is maximum, is set as the frequency used in frequency setting step S4 and AC supply step S5. This enables setting of a frequency with a one-time manipulation to cause the output from AC bridge circuit 20 to increase in response to objects under inspection M with differing surface processing states, shapes, and impedances. Optimal frequency changes with object under inspection material, shape, and surface processing state, but when these are known in advance, setting the frequency is unnecessary. Thus a sensitive response to changes in surface processing state is possible, and inspection sensitivity can be improved.

Here, frequency setting step S3 can also be executed before variable resistor setting step S2. When reference test piece S is used, an optimal frequency can be selected and at least a little more of the inherent properties of object under inspection M can be extracted, but it is also possible to use a reference test object in lieu of reference test piece S to set the frequency.

In threshold setting step S4, reference test piece S is brought into proximity with inspection detector 23, and AC power at the frequency set in frequency setting step S3 is supplied from AC power supply 10 to AC bridge circuit 20. The voltage output from AC bridge circuit 20 is amplified by amplifier 31; a full wave rectification is performed in absolute value circuit 32, a DC conversion is performed in LPF 33, and the result is output to judgment means 36. The output value output to judgment means 36 when a reference test piece S with known good surface processing is brought into proximity with inspection detector 23 is set as the normal threshold value and stored in judgment means 36. Here, the output value output to judgment means 36 when a reference test object is brought into proximity with inspection detector 23 is set as a bad threshold value, and the convenience of the inspection can be increased by increasing the threshold value.

In pass/fail judgment step S8, described below, the output value when object under inspection M is brought into proximity with inspection detector 23 is compared to the normal threshold value and the bad threshold value, and when a pass/fail for object under inspection M is judged, a pass/fail for the output value of object under inspection M cannot be judged when the output value of object under inspection M is between the normal threshold value and the bad threshold value. It is also possible therefore to measure output using multiple reference test objects with differing surface states, and to set the bad threshold value so that the difference relative to the normal threshold value become small. It is also acceptable to determine the bad threshold value more precisely by concurrently using destructive testing of the object under inspection.

In AC supply step S5, AC power at the frequency set in frequency setting step S3 is supplied from AC power supply 10 to AC bridge circuit 20. Here reference test piece S is not in close proximity to inspection detector 23.

Next, in disposition step S6 the object under inspection M for which a determination of pass/fail for the surface processing state is to be determined is brought into proximity with inspection detector 23 and an eddy current is excited in the object under inspection. At this point, a voltage output signal is output from AC bridge circuit 20; the output signal is amplified by amplifier 31, full wave rectified by absolute value circuit 32, and converted to DC by LPF 33.

Before object under inspection M approaches inspection detector 23, or after disposition of object under inspection M, the surface temperature of object under inspection M is measured by temperature sensor 38 and an object under inspection M surface temperature signal is output to judgment means 36.

In test state judgment step S7, a comparison is made by phase comparator 34 between the AC power waveform supplied from AC power supply 10 and the AC voltage waveform output from AC bridge circuit 20, and their phase differences are detected. By monitoring this phase difference, a pass/fail judgment can be made of the test state (e.g., that there is no positional offset between inspection detector 23 and object under inspection M). Even if outputs from AC bridge circuits 20 are the same, when the phase difference varies greatly there is a change in test state, and a judgment can be made the test may not be being correctly implemented. In addition, when the temperature of object under inspection M detected by temperature sensor 38 is within a predetermined range, judgment means 36 makes a pass/fail judgment of the surface processing state of object under inspection M; when the temperature detected by temperature sensor 38 is outside a predetermined range, no pass/fail judgment is made of the surface processing state of object under inspection M. Here the predetermined temperature range is a temperature range over which temperature changes in object under inspection M substantially do not affect the test; they can be set, for example to 0~60° C. Various measures can be undertaken when the temperature of the surface of object under inspection M is outside a predetermined temperature range, such as causing the system to stand by until object under inspection M falls within a predetermined temperature range, or blowing air onto object under inspection M, or moving object under inspection M to a different line without testing it.

In pass/fail judgment step S8, the signal converted to DC by LPF 33 is input to judgment means 36; judgment means 36 judges the pass/fail state of the surface of object under inspection M based on the inputted signal. I.e., this step is an evaluation step for evaluating the surface properties of the object under inspection based on the output signal output from AC bridge circuit 20. The judgment results by judgment means 36 are displayed by display means 37, and if the surface state is bad, a warning is issued.

The judgment of the object under inspection M surface processing pass/fail state is carried out by comparing the output value (measurement value) from LPF 33 with the normal threshold value set in threshold setting step S4. When setting a bad threshold value, the output value (measurement value) from LPF 33 is compared to the normal threshold value and the bad threshold value.

With the above-described steps, a pass/fail test of the surface processing state of object under inspection M can be tested easily and with high accuracy. To continue the test, it is sufficient to exchange only object under inspection M and repeat disposition step S6, test state judgment step S7, and pass/fail judgment step S8. If the type of object under inspection M or the type of surface processing etc. is changed, variable resistor setting step S2, frequency setting step S3, and threshold setting step S4 are again carried out.

Inspection detector 23 indirectly captures surface resistance changes by capturing changes in eddy currents flowing on the surface of gear G. Here, if shot-peening is performed as surface processing, causes for change in eddy current flow would include deformations, structural refinement, or dislocation caused by shot-peening, but these are essentially fixed under the temperature changes within the measurement environment (0° C.~40° C.). Magnetic changes detected by inspection detector 23 are caused by changes in the demagnetized field of eddy current flow, and given that causes of changes in eddy current flow are little affected by temperature changes in the measurement environment, effects on test accuracy from temperature changes can be minimized. Note that since a reference state is detected by reference detector 22, a reference test piece S for outputting a reference output may be used. Thus, for example, by using a reference test object S with a known good surface processing state, pass/fail of the surface state of object under inspection M can be evaluated by comparison with the reference test object S.

Thus by bringing reference test piece S into proximity with reference detector 22 (disposing reference test piece S inside coil 22b of reference detector 22) to obtain a reference output, the pass/fail of the surface state of object under inspection M can be evaluated with good accuracy. However, depending on the setting environment of the surface property inspection apparatus, it may be difficult to maintain the temperature of object under inspection M and temperature of reference test piece S at the same level. Also, depending on the setting environment, the induced noise and disturbance received by object under inspection M and reference test piece S respectively may differ enormously between object under inspection M and reference test piece S. In these cases, it actually becomes more difficult to accurately evaluate the surface of object under inspection M using reference test piece S, therefore it is desirable to evaluate surface properties without using reference test piece S.

Thus if it is assumed that surface properties are tested without the use of reference test piece S, the reference detector 22 coil 22b can be made more compact than inspection detector 23 coil 23b. This enables reference detector 22 to be made more compact. If reference detector 22 coil 22b is made compact, a ferromagnetic core 22a is disposed inside coil 22b. Placement of a ferromagnetic core 22a causes inductance in reference detector 22 coil 22b to rise, therefore if an applied voltage of the same frequency is used, inductance is higher than with a coil in which no ferromagnetic core 22a is disposed. Therefore coil 22b with an inductance approximately the same as inspection detector 23 coil 23b can be made more compact.

Also, by disposing ferromagnetic core 22a inside reference detector 22 ferromagnetic coil 22b, this becomes a magnetic shield, with the advantage of being less susceptible to induced noise effects from the periphery of coil 22b. In addition, by making the reference detector 22 coil 22b compact, it also becomes possible to place this coil 22b on a printed circuit board on which an AC bridge circuit (variable resistor 21) is mounted. This enables reference detector 22 to be easily handled together with the AC bridge circuit, and improves freedom when installing the surface property inspection apparatus.

Surface Property Test System: First Embodiment

Next, including surface property inspection apparatus 1, we discuss a surface property evaluation system for evaluating the surface properties of an object under inspection either in-line or out-line in a surface processing step using a shot-peening apparatus for performing shot-peening as surface processing. As shown in FIGS. 4A~4D and FIGS. 5A~5D, surface property evaluation system 100 is furnished with a surface processing apparatus 110 for performing surface processing of object under inspection M, a first transport mechanism 120 comprising a cylinder, a second transport mechanism 121 comprising a transport arm, a third transport mechanism 122 comprising a conveyor, and a test detector transport mechanism 123 comprising a cylinder. Note that in FIGS. 4A~4D and FIGS. 5A~5D, plan views and side views are shown at top and bottom. In the plan views of FIGS. 4A, 4B, and 5D, a diagram of inspection detector 23 is omitted. Also, inspection detector 23 is included in surface property inspection apparatus 1, but is separately shown in FIGS. 4A~4D and FIGS. 5A~5D for purpose of explanation. In the present embodiment, shot-peening of the gear portion of gear G is performed as the surface processing. Here surface property evaluation system 100 has the constitution shown in claims 9 and 10, including the surface property inspection apparatus shown in Claim 4.

Note that in the present embodiment first transport mechanism 120 is provided in surface property inspection apparatus 1, but a configuration may also be adopted in which it is provided in surface property evaluation system 100.

First transport mechanism 120 enables object under inspection gear G to be driven up or down, and is furnished at its tip with a registration portion 120a for registering a position inside the horizontal plane when transporting gear G. Registration portion 120a is formed, for example, as a protuberance having an upward facing taper, and is constituted to be able to register simply by loading gear G. First transport mechanism 120 is capable of transporting gear G in an up or down direction relative to the evaluation position Ts (one or both positions on the up or down side of evaluation position Ts) at which gear G is tested inside inspection detector 23 coil 23b. Thus registration portion 120a is a registration portion for registering the position of the object under inspection in the horizontal plane when the first transport mechanism transports an object under inspection. Note that the registration portion is not limited to this constitution, but may have any constitution capable of registering an object under inspection in a horizontal plane. For example, it may have a constitution in which stopper 122a, described below, has a registering function.

Second transport mechanism 121 comprises a transport arm capable of gripping gear G; it transports gear G, moved by first transport mechanism 120 to a first standby position T1, described below, in a horizontal direction, and transports gear G to surface processing apparatus 110 stage 115a. Note that depending on the positional relationship between first standby position T1 and surface processing apparatus 110 stage 115a, second transport mechanism 121 can use a mechanism for transporting gear G in a direction which is inclined relative to the horizontal direction.

Third transport mechanism 122 transports from pre-shot-peening area Ab via second standby position T2 to shot-peening and test-completed area Aa.

Test detector transport mechanism 123 moves inspection detector 23 up or down, such that gear G is positioned at the evaluation position Ts of inspection detector 23.

Figure 6A:
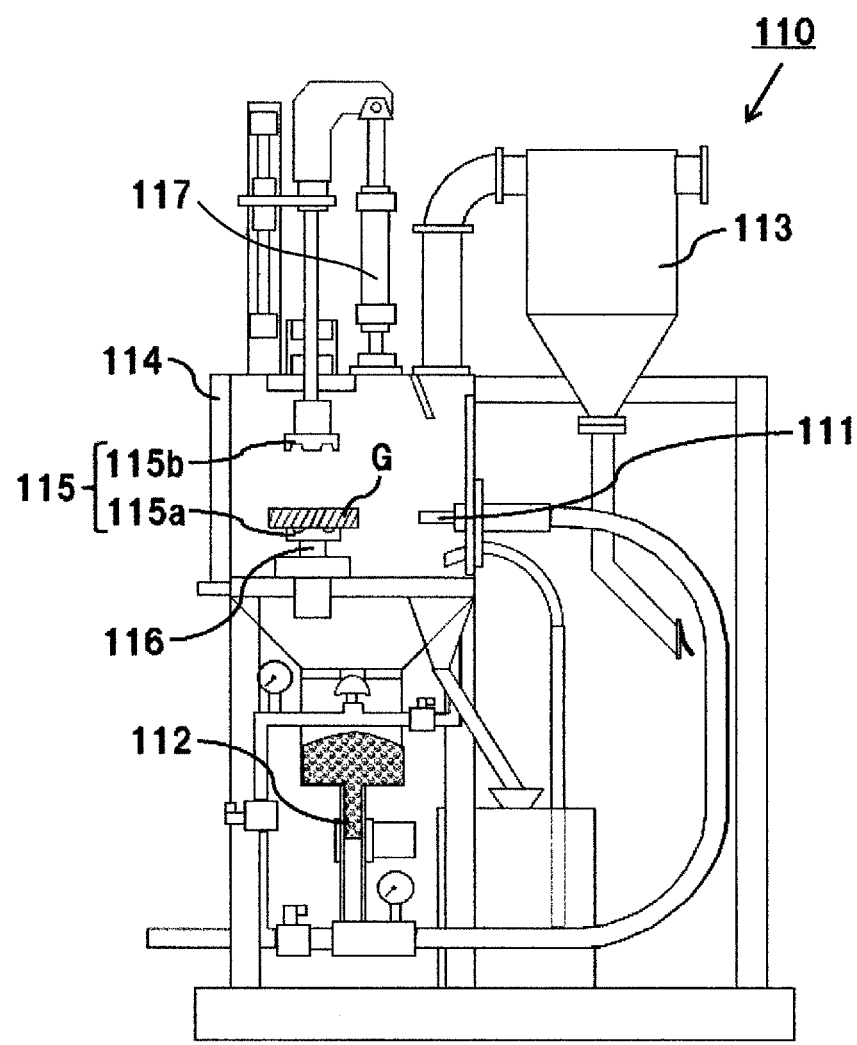
FIG. 6A is an explanatory diagram showing the constitution of a surface processing apparatus.

In the present embodiment, a shot-peening apparatus is used as surface processing apparatus 110. As shown in FIG. 6A, a shot-peening apparatus is furnished with a spray nozzle 111 for shot-peening by spraying out a projectile material onto the object under inspection, a supply apparatus 112 for supplying projectile material to spray nozzle 111, and separation apparatus 113 for sorting and separating between projectile material, powder dust, etc., whereby shot-peening is performed inside a processing chamber 114. Also provided are a holding portion 115 comprised of a stage 115a for loading gear G in a registered state on stage 115a and a work retainer 115b for pressing on and affixing gear G from above, and a rotation apparatus 116 linked to stage 115a for rotating gear G in a horizontal direction.

Figure 6B:
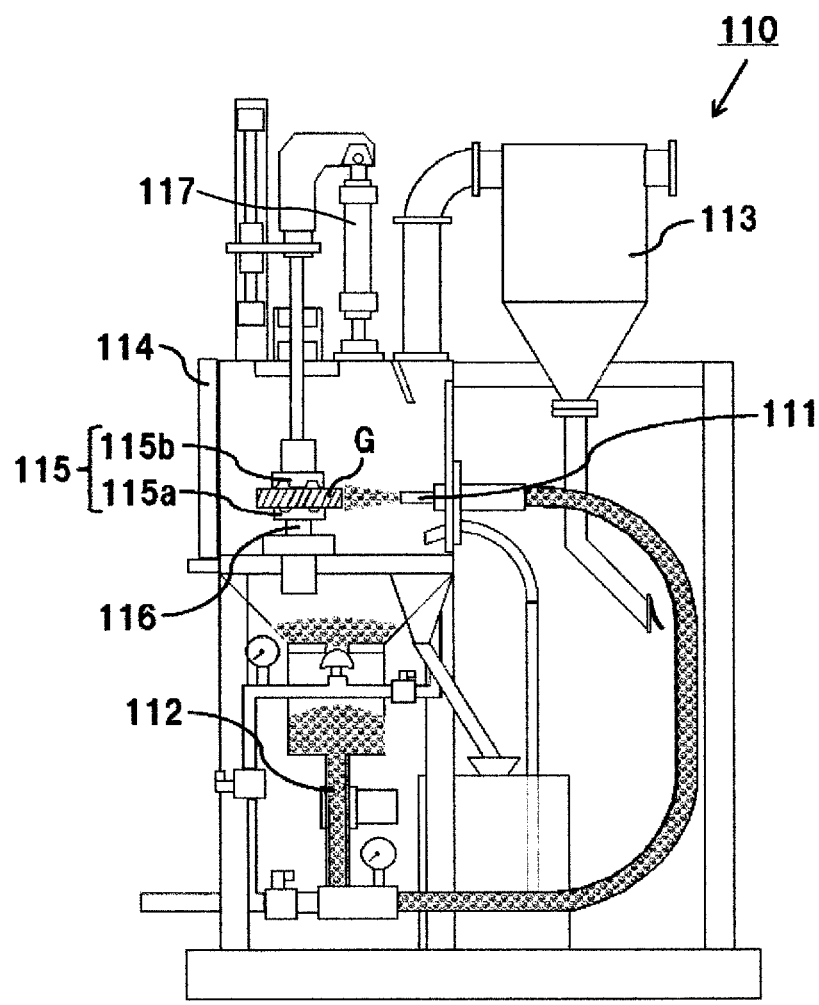
FIG. 6B is an explanatory diagram showing the constitution of a surface processing apparatus.

Shot peening by surface processing apparatus 110 is implemented, as shown in FIG. 6B, by first moving work retainer 115b downward using cylinder 117, pressing and affixing from above gear G transported to stage 115a, and shot-peening the gear portion of gear G from the tooth side by spraying projectile material from spray nozzle 111 while rotating gear G using rotation apparatus 116.

Figure 4A:
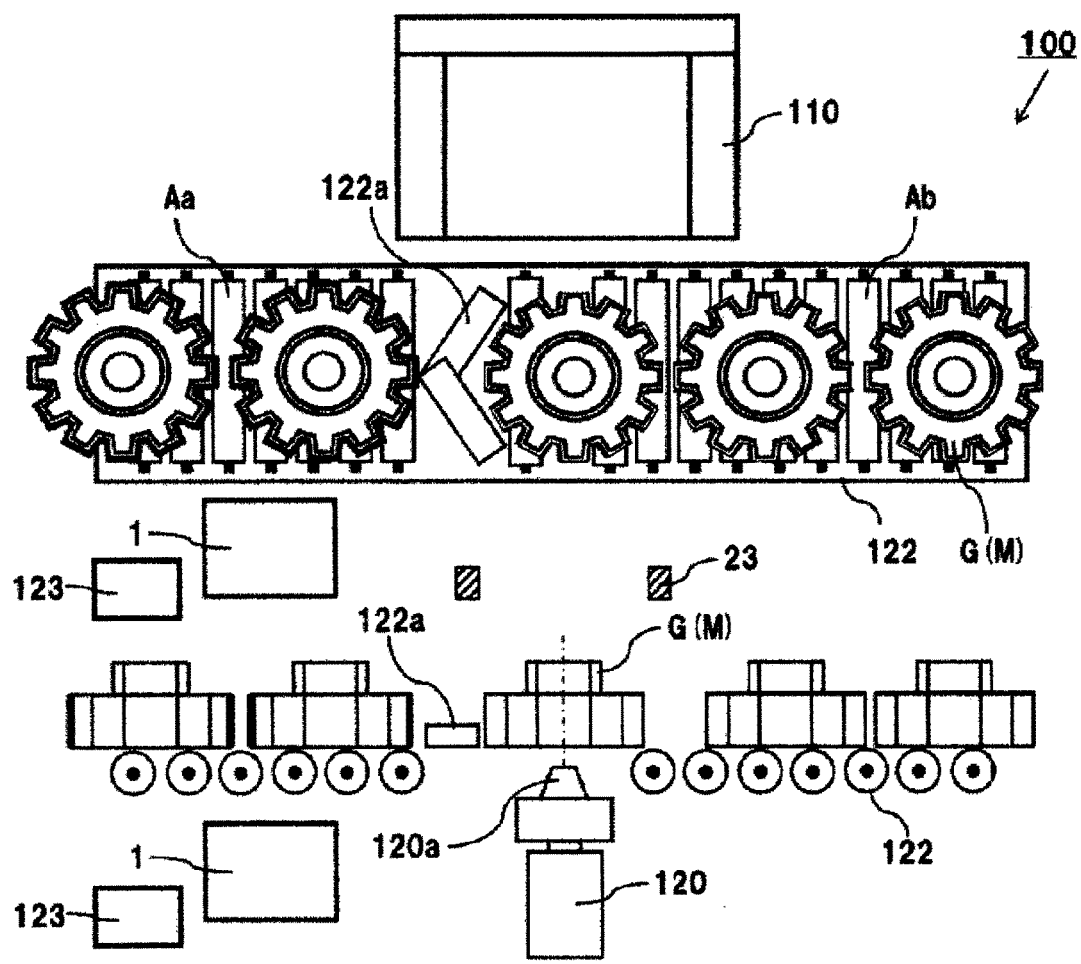
FIG. 4A is an explanatory diagram showing the constitution of a surface property inspection system and steps of a surface property inspection method in a first embodiment.

We now explain a method for evaluating the surface properties of gear G using surface property evaluation system 100. First, as shown in FIG. 4A, cylindrical gear G is transported with its shaft in a plumb position from shot-peening area Ab by third transport mechanism 122, and gear G is stopped by stopper 122a.

Figure 4B:
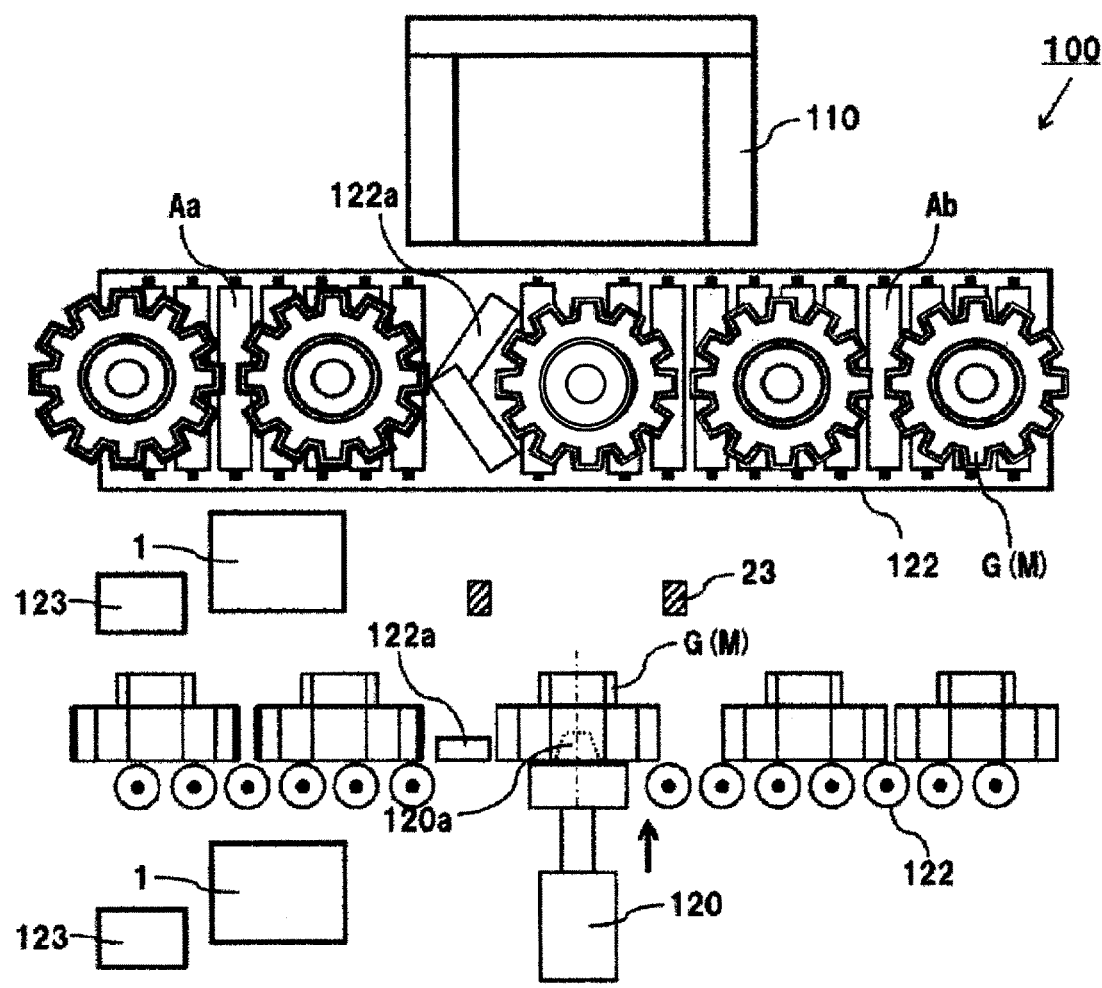
FIG. 4B is an explanatory diagram showing the constitution of a surface property inspection system and steps of a surface property inspection method in a first embodiment.

Next, as shown in FIG. 4B, first transport mechanism 120 raises gear G from below and registers gear G at second standby position T2. Here, receiving hardware furnished with a taper capable of penetrating a hole portion at the center of gear G may, for example, be used as a registration mechanism.

Figure 4C:
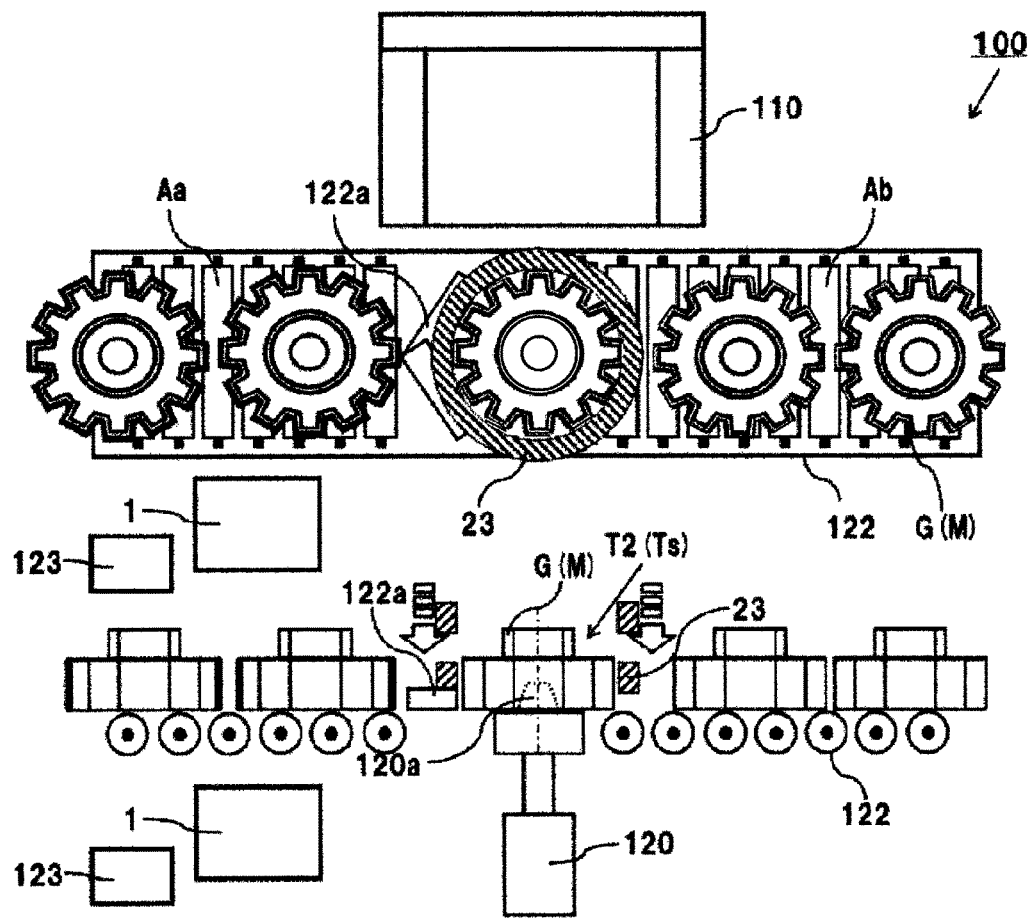
FIG. 4C is an explanatory diagram showing the constitution of a surface property inspection system and steps of a surface property inspection method in a first embodiment.

Next, as shown in FIG. 4C, inspection detector 23 is moved to the gear G side by test detector transport mechanism 123, coil 23b is disposed at a position facing the gear portion, and the pre-surface processing surface properties are tested. Pre-surface processing surface property data is stored in evaluation device 30 judgment means 36. Since gear G is registered by registration portion 120a, gear G can be positioned at an appropriate position when evaluating surface properties, therefore a high accuracy inspection can be reliably performed. Here, second standby position T2 becomes the evaluation position Ts at which surface properties are evaluated and inspected. In the present embodiment, second standby position T2 serves as evaluation position Ts, but a configuration may also be adopted in which second standby position T2 is positioned either on the top side or the bottom side of evaluation position Ts.

Figure 4D:
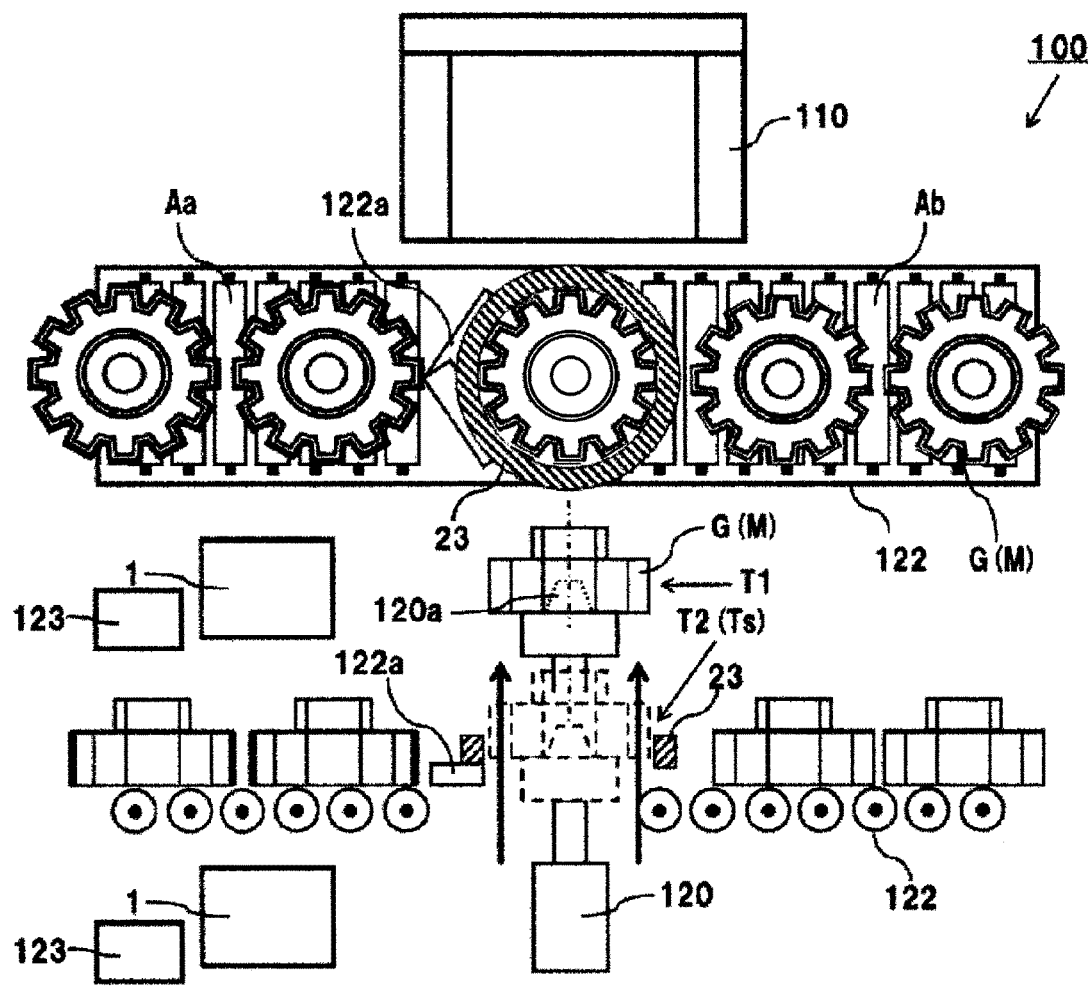
FIG. 4D is an explanatory diagram showing the constitution of a first embodiment surface property inspection system and surface property inspection method.

Next, as shown in FIG. 4D, gear G is moved by first transport mechanism 120 to first standby position T1 above inspection detector 23. Thus gear G is moved from inspection detector 23 evaluation position Ts and can be transported to surface processing apparatus 110. In the present embodiment first standby position T1 is on the top side of evaluation position Ts, but it is sufficient for it to be in a position either above or below evaluation position Ts and facing surface processing apparatus 110.

Figure 5A:
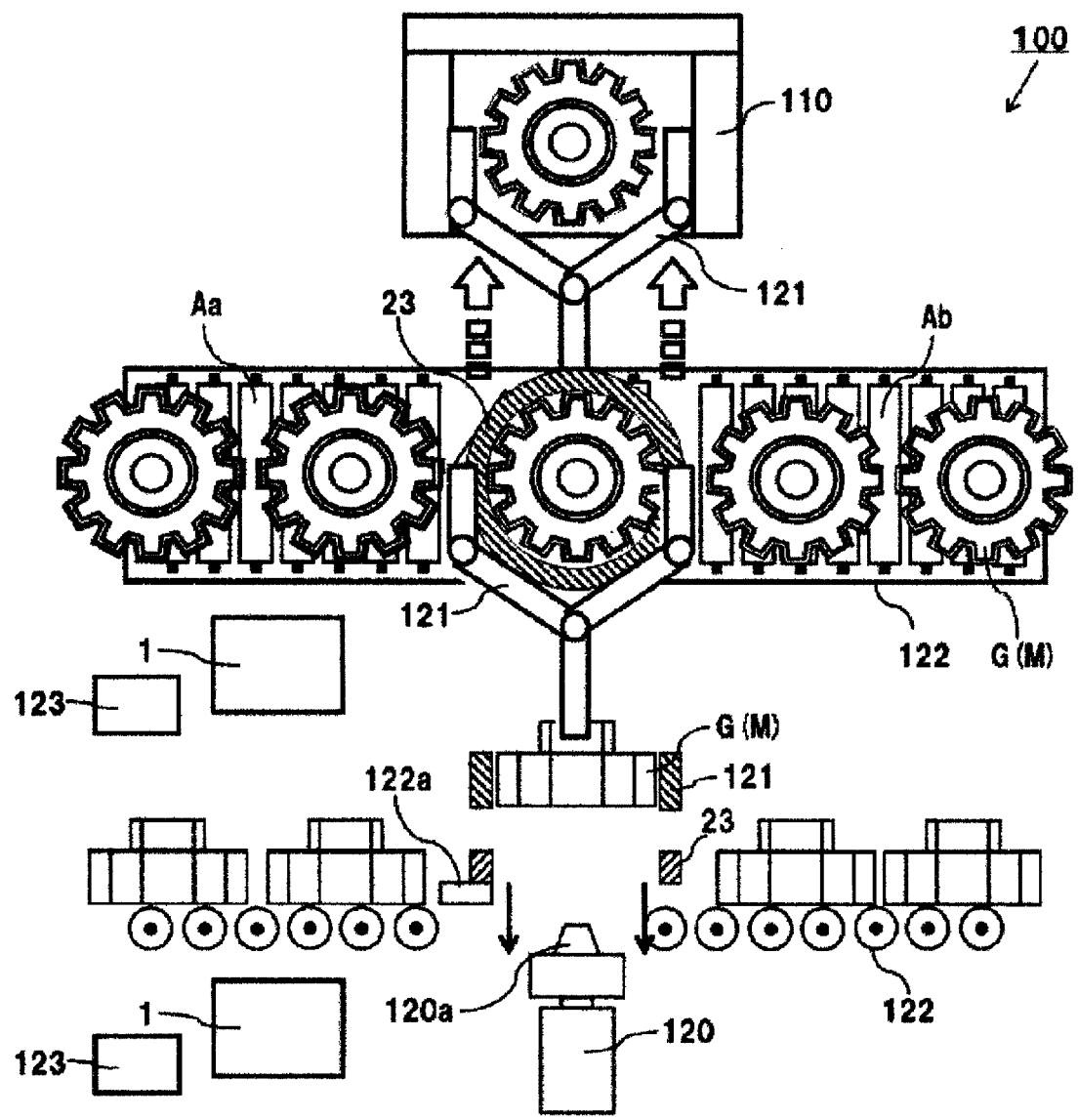
FIG. 5A is an explanatory diagram showing the constitution of a first embodiment surface property inspection system and surface property inspection method.

Next, as shown in FIG. 5A, gear G is gripped by second transport mechanism 121, transported to surface processing apparatus 110, loaded onto stage 115a positioned in a horizontal direction or a direction inclined relative to horizontal as seen from first standby position T1, and registered and affixed by work retainer 115b.

Figure 5B:
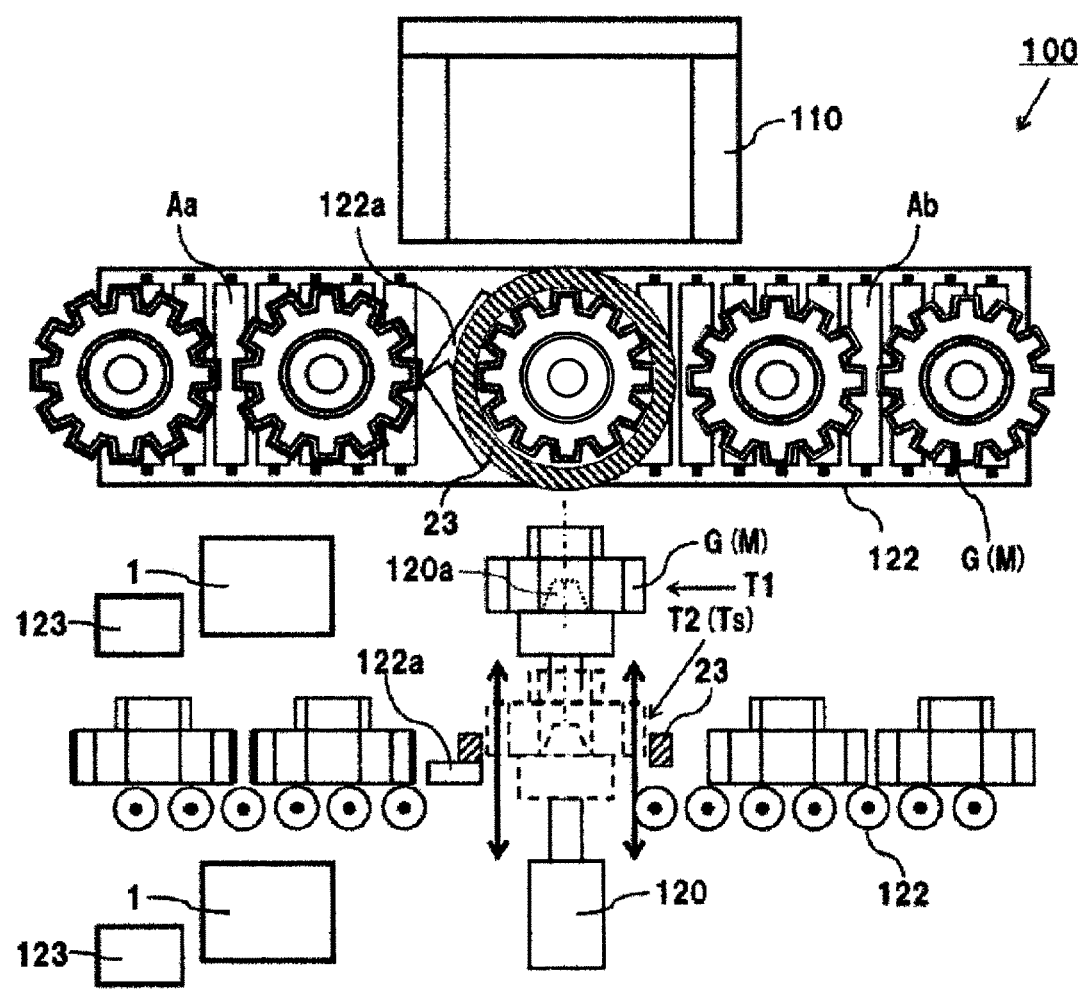
FIG. 5B is an explanatory diagram showing the constitution of a first embodiment surface property inspection system and surface property inspection method.

After surface processing by surface processing apparatus 110, as shown in FIG. 5B gear G is gripped by and transported to registration portion 120a of first transport mechanism 120 standing by at first standby position T1, by second transport mechanism 121. Next, gear G is moved by first transport mechanism 120 to second standby position T2 (evaluation position Ts) and post-surface processing surface properties are inspected. Here evaluation device 30 compares pre-surface processing surface property data stored in judgment means 36 with post-surface processing surface property data and makes a pass/fail judgment of the surface processing state by comparison with a previously set threshold value.

Figure 5C:
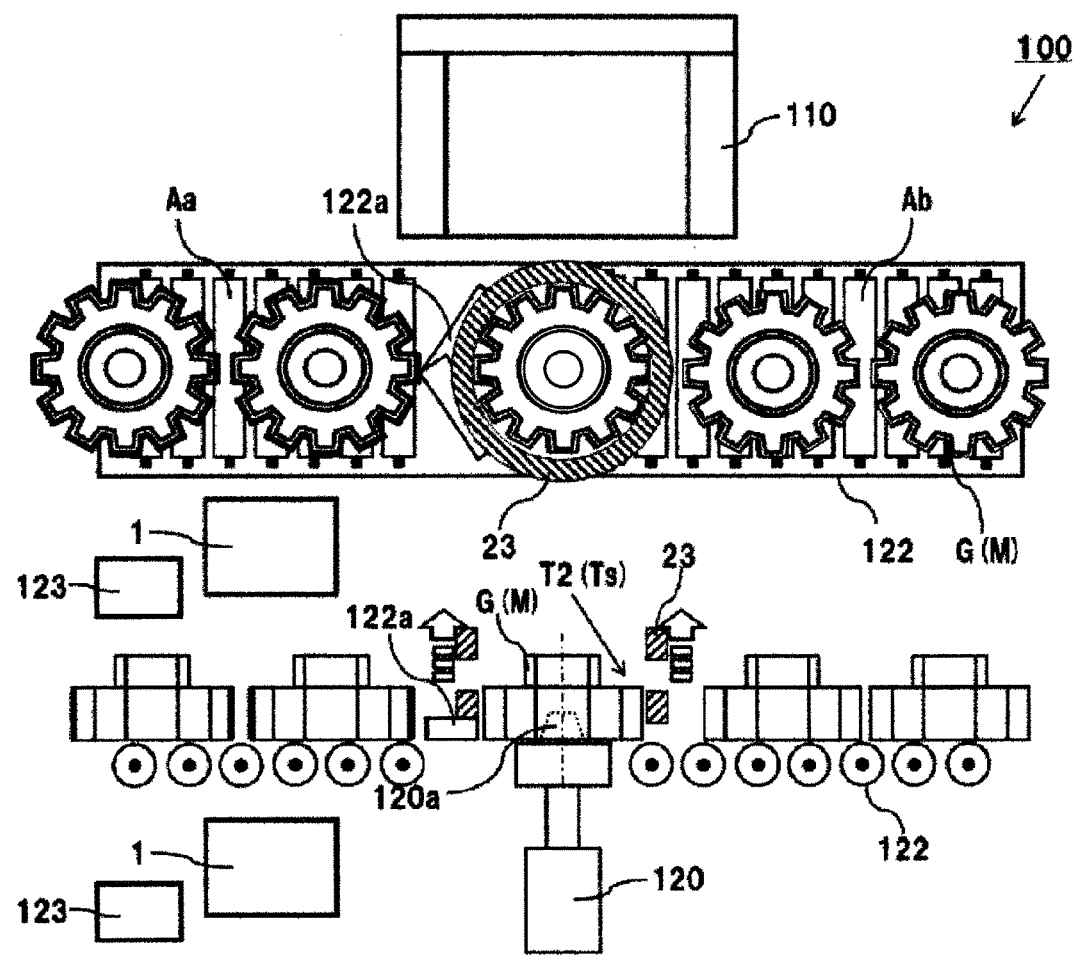
FIG. 5C is an explanatory diagram showing the constitution of a first embodiment surface property inspection system and surface property inspection method.
Figure 5D:
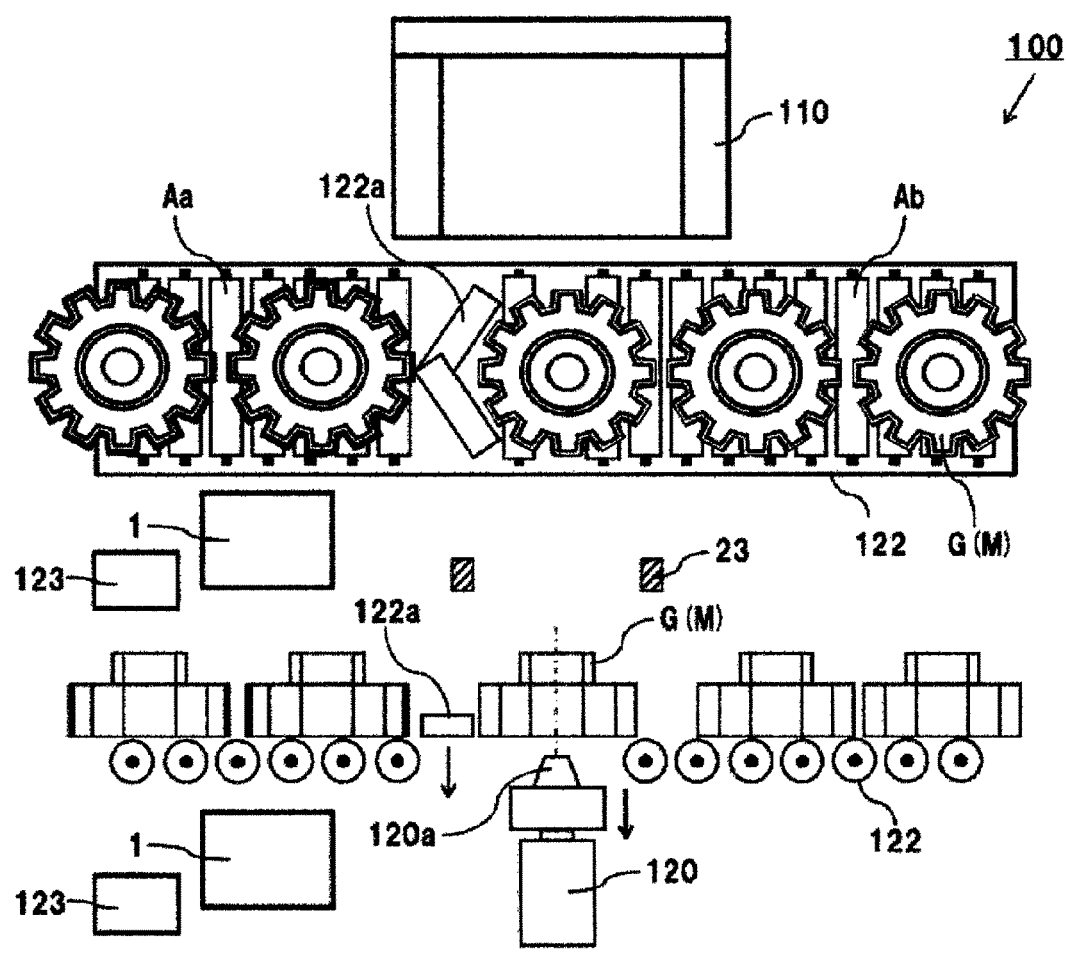
FIG. 5D is an explanatory diagram showing the constitution of a first embodiment surface property inspection system and surface property inspection method.

Next, as shown in FIG. 5C, inspection detector 23 is raised by test detector transport mechanism 123 and gear G is caused to separate; as shown in FIG. 5D, stopper 122a is released and gear G is transported to inspection-completed area Aa by third transport mechanism 122.

As shown in the steps above, in a surface property evaluation system 100 including a surface processing apparatus 110, a registration portion 120a is provided on first transport mechanism 120, therefore gear G can be positioned at an appropriate position when evaluating surface properties, so a high accuracy inspection can be reliably performed. Gear G can be transported in an appropriate state to second transport mechanism 121 by first transport mechanism 120 furnished with registration portion 120a, and transport to an appropriate position of surface processing apparatus 110 by second transport mechanism 121 can be achieved. I.e., positioning can be effected by a surface property inspection apparatus 110 with a simple structure. An pre- and post-shot-peening inspection in which the object under inspection is automatically transported can be achieved by the combination of first transport mechanism 120, second transport mechanism 121, and test detector transport mechanism 123, enabling an in-line inspection matched to the seisankosu on the shot-peening line.

In the step above, as shown in FIG. 4C, a pre-surface processing surface property inspection was conducted, but it a post-surface processing surface property inspection alone is sufficient. In that case, the pass/fail judgment of the surface processing state is performed by comparing a measured value to a normal threshold value, or a measured value to a normal threshold value and a bad threshold value.

Figure 7:
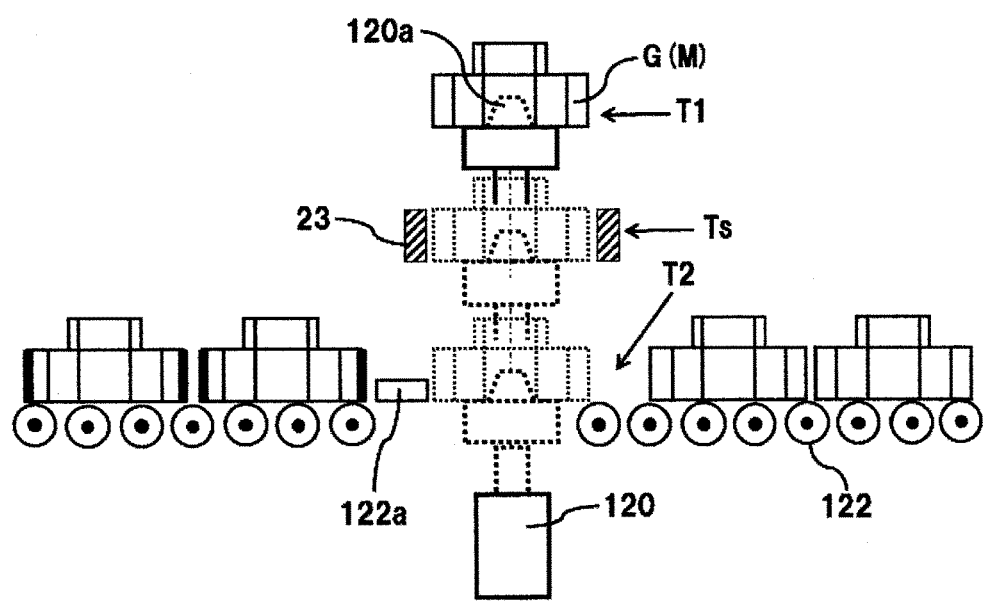
FIG. 7 is an explanatory diagram showing a variant example of a first embodiment surface property evaluation system.

Inspection can also be performed by moving only gear G, with the position of inspection detector 23 in a fixed state. In that case, as shown in FIG. 7, inspection detector 23 is disposed between first standby position T1 and second standby position T2, and second standby position T2 is placed in a position below evaluation position Ts, while first standby position T1 is place in a position above evaluation position Ts. Gear G, transported up to second standby position T2, is moved upward by first transport mechanism 120 to be positioned at the inspection detector 23 evaluation position Ts. An inspection can be performed by moving only the object under inspection with the inspection detector 23 position fixed, making it unnecessary to provide an inspection detector transport mechanism 123, and reducing the likelihood of positioning error. Note that inspection detector 23 is affixed by a supporting affixing fixture (e.g. multiple resin rod members), but a diagram of this is omitted in FIG. 7.

Surface Property Test System: Second Embodiment

Figure 8A:
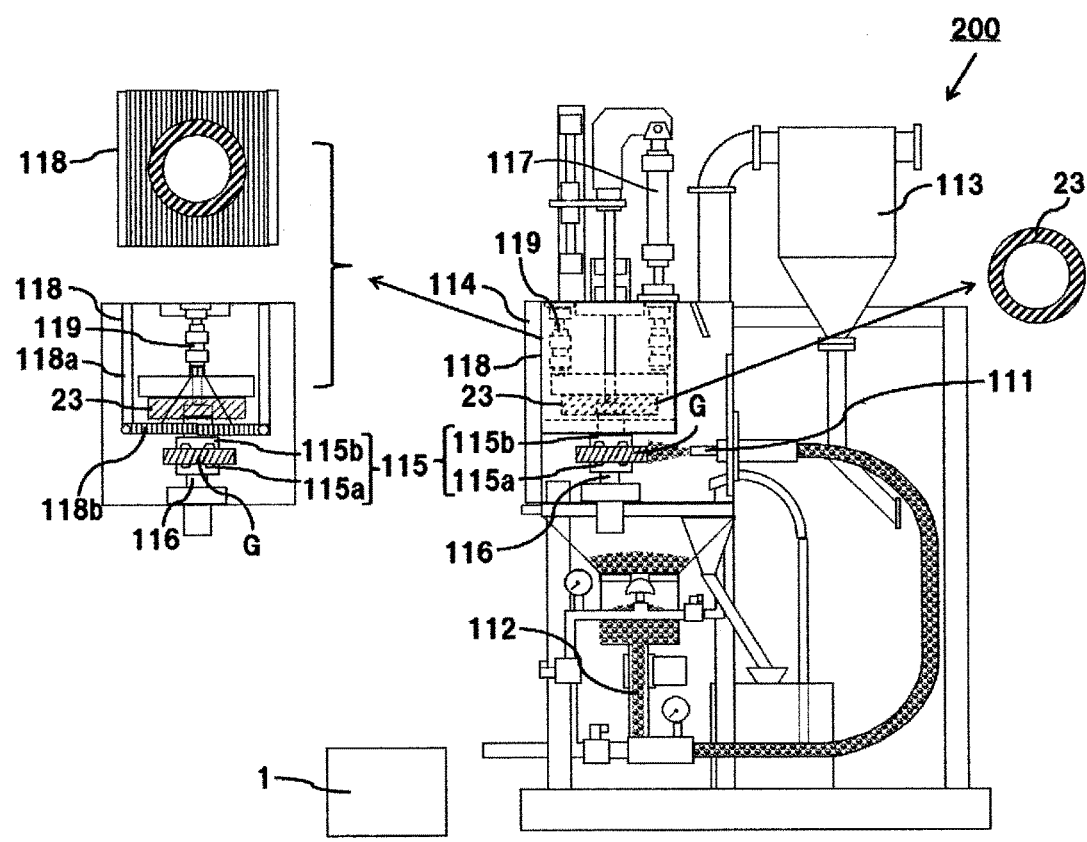
FIG. 8A is an explanatory diagram showing the constitution of a second embodiment surface property inspection system and surface property inspection method.
Figure 8B:
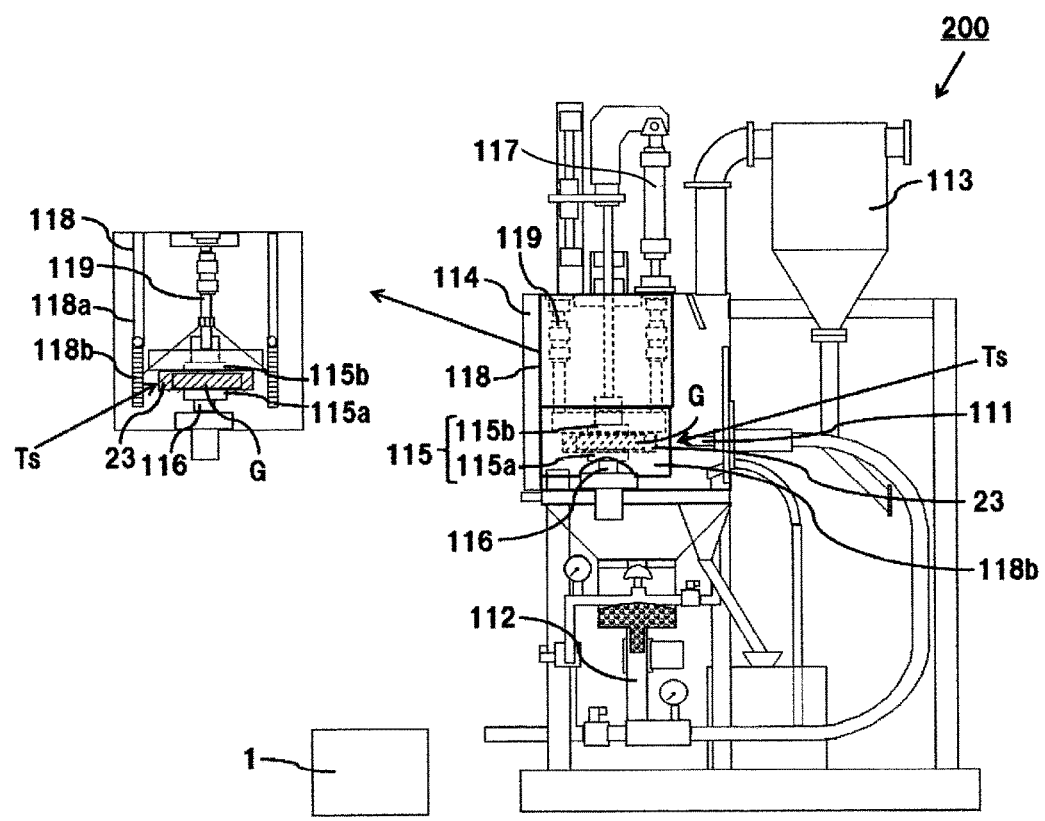
FIG. 8B is an explanatory diagram showing the constitution of a surface property inspection system and steps of a surface property inspection method in a first embodiment.

As shown in FIGS. 8A and 8B, a surface property evaluation system 200 is built into inspection detector 23 inside processing chamber 114 of surface processing apparatus 110. Note that in FIGS. 8A and 8B, a diagram of the mechanism for transporting object under inspection M to surface processing apparatus 110, such as second transport mechanism 121 or third transport mechanism 122, is omitted.

FIG. 8A shows the state in which shot-peening is being applied to gear G. To explain the structure and operation of detector protective panel 118, in FIG. 8A we include a plan view of the region close to detector protective panel 118 and a front elevation seen from the left side of the figure. Inspection detector 23 is connected to cylinder 119, which transports inspection detector 23 and is a moving mechanism for positioning gear G at evaluation position Ts inside coil 23b, and is disposed above gear G, coaxial with the gear G shaft. Outside inspection detector 23 a detector protective panel 118 is placed to protect inspection detector 23 when carrying out shot-peening. Detector protective panel 118 comprises a affixing panel 118a placed so as to cover the side surface of inspection detector 23, and a movable panel 118b, placed so as to cover the bottom surface thereof.

Movable panel 118b has a rotational center at one edge on the affixing panel 118a side, and is suspended by a chain or metal wire in the part distant from the rotational center. When base end of this chain or metal wire is driven by cylinder 119 so that the bottom is closed off, a switch is made to a state in which the bottom is opened. When shot-peening, the bottom is in a closed state to protect inspection detector 23.

FIG. 8B shows the state in which, after shot-peening, an inspection is made of the surface properties of gear G. FIG. 8B includes a front elevation diagram around detector protective panel 118. Inspection detector 23 is transported by cylinder 119 toward the evaluation position Ts of gear G held by holding portion 115. Here the movable panel 118b, which had been covering the bottom surface of inspection detector 23, is rotated so that the bottom opens, and does not interfere with the inspection detector 23 descending on the bottom side.

The above-described constitution enables rapid inspection of gear G after shot-peening. A holding portion 115 is provided to hold gear G in its registered state, thereby enabling the object under inspection to be positioned at an appropriate position when evaluating surface properties, so that a high accuracy inspection can be performed. Holding portion 115 also permits automation, making in-line inspection becomes possible. Because a detection device can be packaged with surface property inspection apparatus 110 and provided to customers, the value of surface treatment apparatus 110 can be increased, as can customer satisfaction. In addition, because projectile material can be prevented by detector protective panel 118 from colliding with inspection detector 23, the life of inspection detector 23 can be extended and false detections caused by damage to inspection detector 23 can be prevented.

If there is little bounce back of the projectile material, or inspection detector 23 can be removed to a place position where there is virtually no bounce back of projectile material, then it is not necessarily required that detector protective panel 118 be erected.

Variant Examples

When inspecting members having gear portions on the inner circumferential surface, it is desirable for inspection detector 23 to have a shape capable of insertion through the member so that coil 23b can be disposed to oppose the inner circumferential surface.

Figure 9:
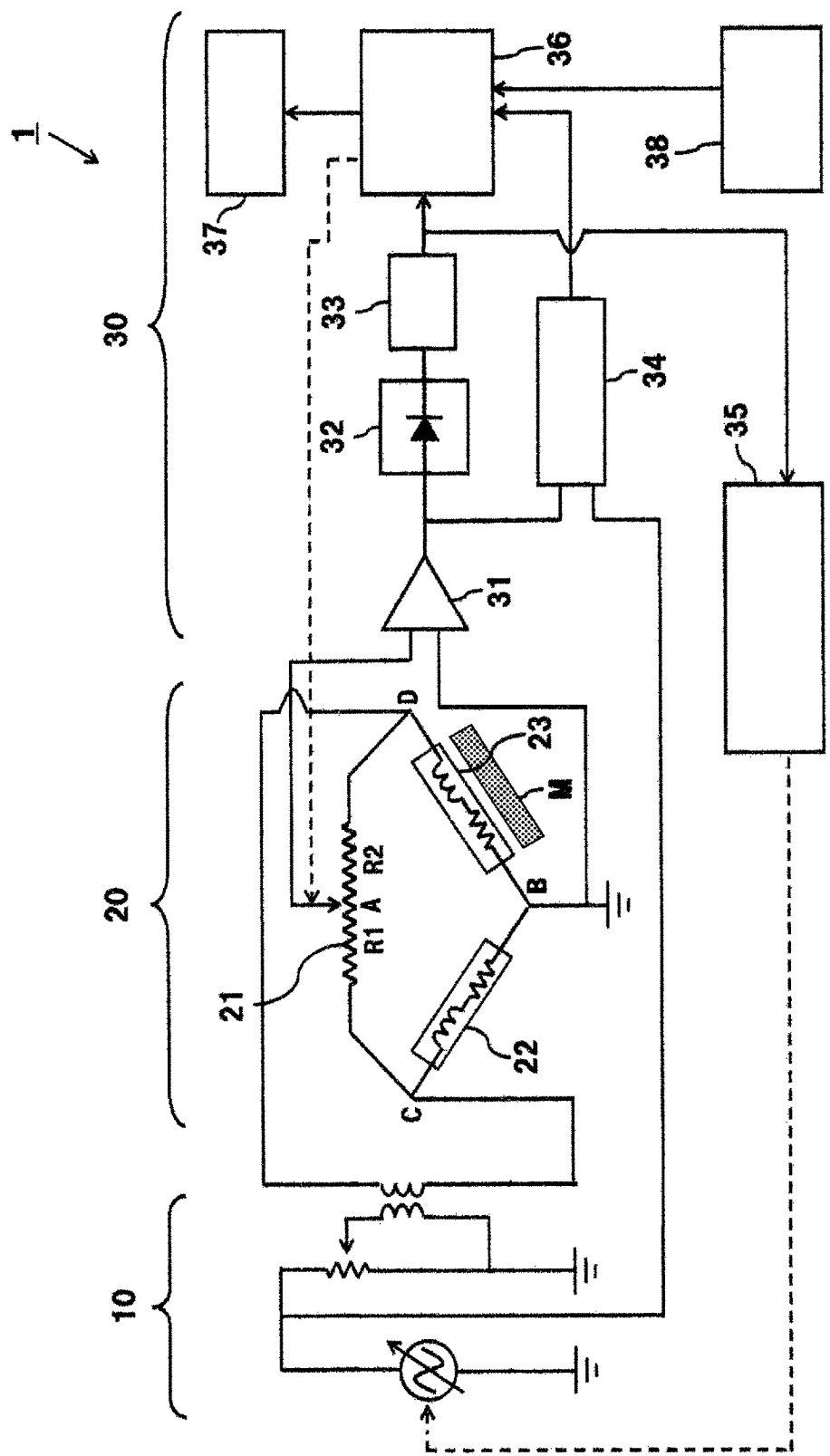
FIG. 9 is an explanatory diagram showing a variant example of the circuit configuration in a surface property inspection apparatus.

As shown in FIG. 9, a configuration in which amplifier 31 is connected to point A and point B and AC power supply 10 is connected to point C and point D may also be used as the circuit configuration of AC bridge circuit 20.

When test state judgment step S7 is not implemented, surface property inspection apparatus 1 can omit phase comparator 34. For example, a configuration can be used in which the positional relationship between inspection detector 23 and object under inspection M is performed by a position detection means such as a laser displacement gauge and determine, using an opto-electric sensor (laser) or the like, whether the offset between the inspection detector 23 axis and the object under inspection M axis is within a predetermined range. Phase comparator 34, frequency adjuster 35, or display means 37 can be integrally disposed by building them in to judgment means 36 or the like.

If the output from AC bridge circuit 20 at the time of object under inspection M measurement is sufficiently large, variable resistor setting step S2 and frequency setting step S3 may be omitted. If omitting frequency setting step S3, surface property inspection apparatus 1 can omit frequency adjuster 35.

Effect of Embodiment

Using the surface property inspection apparatus 1 and surface property inspection method of the present invention, an eddy current is excited in object under inspection M by inspection detector 23 coil 23b, and the surface properties of object under inspection M can be evaluated based on the output signal output from AC power supply 10. This enables high precision inspection of surface state with a simple circuit configuration. Since a method is adopted in which surface properties of the object under inspection are inspected by exciting an eddy current, the effects of temperature variations in the inspection environment can be reduced.

Also, magnetism can be stably supplied to the object under inspection, and the surface property inspection region of the object under inspection can be inspected in one pass. Also, because it is possible to diffuse the eddy current and suppress the emission of heat in the surface of the object under inspection, thermal changes in object under inspection M can be minimized, thereby enabling more accurate inspection.

Using the surface property inspection system of the present invention, an accurate registration of object under inspection M can be performed, and since transport mechanism is provided, in-line inspection is possible in the surface processing step.

Since a surface property inspection apparatus 1 can be packaged with surface processing apparatus 110 and provided to customers, the value of the surface treatment apparatus 110 can be increased, as can customer satisfaction.

Embodiments

An object under inspection in which a gas-carburized cylindrical SCr420 material is shot-peened on its side surface is compared using the surface property inspection method of the present invention with an inspection method in which 7 samples of differing coverage levels are prepared. Coverage here refers to the post-surface processing surface hit mark percentage, and indicates that the large the coverage, the higher is the surface processing density. We varied the inspection environment surrounding temperature from 10~40° C., performed an inspection, and compared outputs.

Figure 10A:
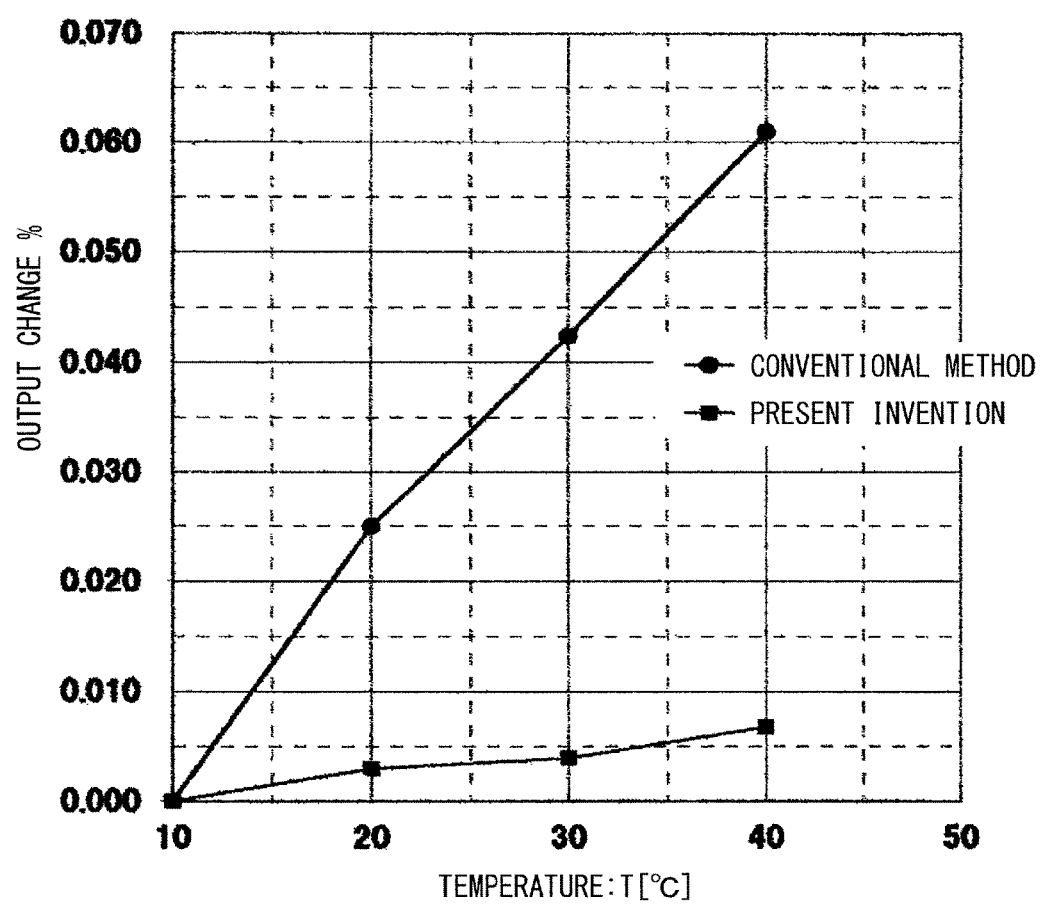
FIG. 10A is an explanatory diagram showing the results of an embodiment comparing the effect of temperature changes in the inspection environment in the surface property inspection method of the present invention with a conventional surface property inspection method.

FIG. 10A is a graph showing the rate of change in amp output caused by surrounding temperature when inspecting a sample with 100% coverage using a reference surrounding temperature of 10° C.; the vertical axis is output change %, and the y axis is the surrounding temperature. It can be seen from this graph that there is less output change caused by temperature with the surface property inspection method of the present invention.

Figure 10B:
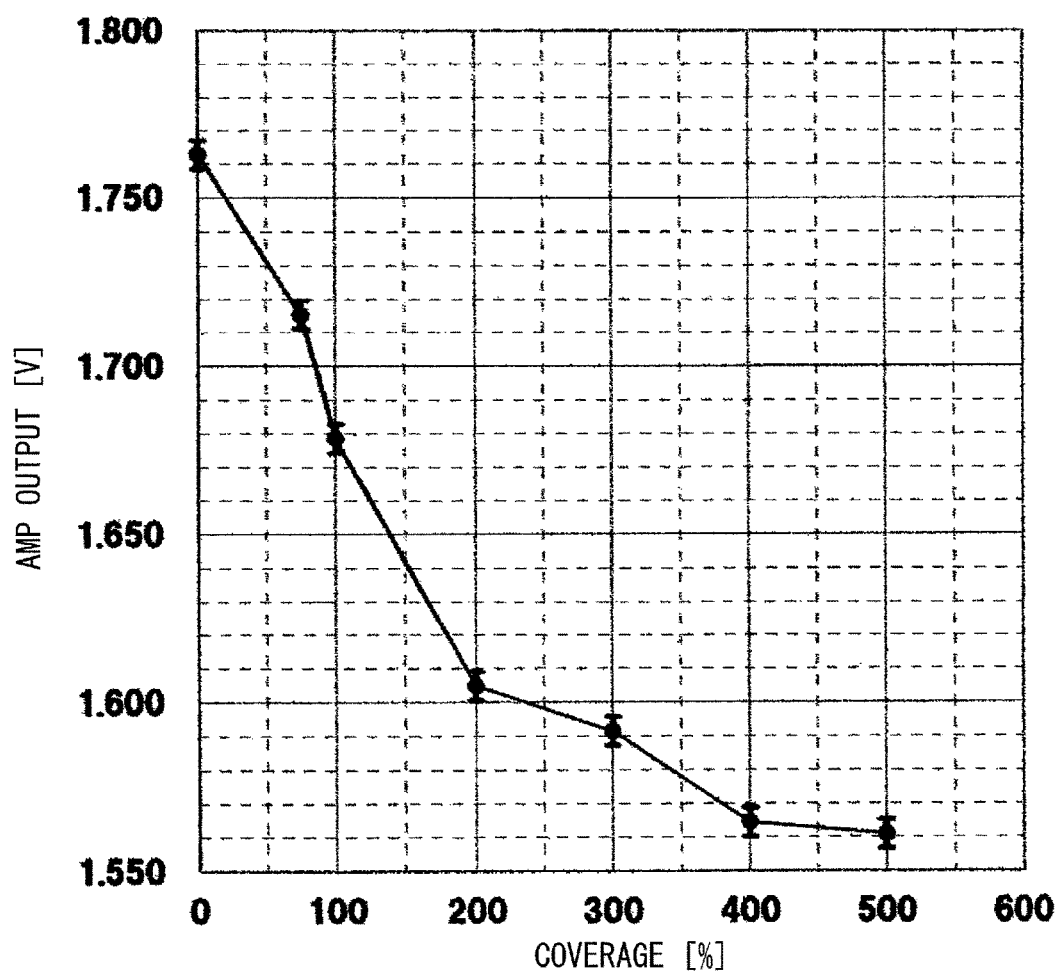
FIG. 10B is an explanatory diagram showing the results of an embodiment comparing the effect of temperature changes in the inspection environment in the surface property inspection method of the present invention with a conventional surface property inspection method.
Figure 10C:
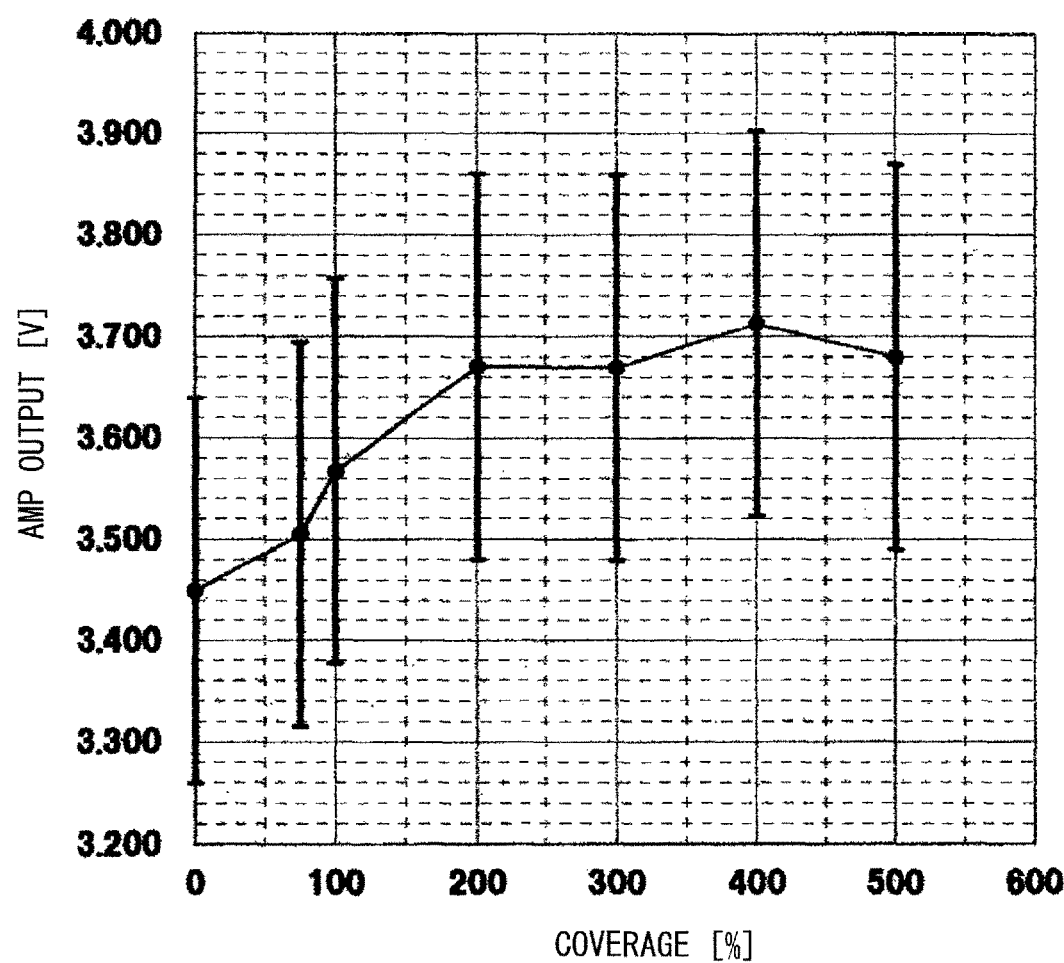
FIG. 10C is an explanatory diagram showing the results of an embodiment comparing the effect of temperature changes in the inspection environment in the surface property inspection method of the present invention with a conventional surface property inspection method.

With temperature caused fluctuate in a range of 10~40° C., the results of inspecting 7 samples with differing coverage standards are shown in FIGS. 10B and 10C. FIG. 10B shows inspection results using the surface property inspection method; FIG. 10C shows inspection results from a conventional surface property inspection method. In each graph, the width of the fluctuation above and below the plot indicates the output fluctuation range when the temperature varied.

As shown in FIG. 10C, in the conventional surface property inspection method there is a high level of output channel variation, and differences in surface properties due to differing coverages cannot be detected. I.e., it is difficult to apply the invention in an in-line environment where temperature changes are severe. On the other hand, as can be seen in FIG. 10B, in the surface property inspection method of the present invention, there is extremely little output variability, and differences in surface properties can be accurately detected.

From the above, it was deter mined that the surface property inspection method of the present invention is little affected by temperature changes in the inspection environment, and it was confirmed that the system could be used favorably for in-line inspection.

What is claimed is:

1. A surface property inspection apparatus for inspecting surface properties of an object under inspection subjected to surface processing, comprising:
an AC bridge circuit;
an AC power supply for supplying AC power to the AC bridge circuit; and
an evaluation apparatus for evaluating the surface properties of the object under inspection based on an output signal from the AC bridge circuit;
wherein the AC bridge circuit has a variable resistor configured so that the distribution ratio is variable between a first resistor and a second resistor, an inspection detector furnished with a coil for creating an AC magnetic field and exciting an eddy current in the object under inspection, and a reference detector for inspecting a reference state serving as reference for comparing with the output from the inspection detector; and whereby the first resistor, the second resistor, the reference detector, and the inspection detector constitute the AC bridge circuit; and
wherein the evaluation apparatus evaluates the surface properties of the object under inspection based on an output signal from the AC bridge circuit, in a state whereby AC power is supplied to the AC bridge circuit, the inspection detector detects an electromagnetic properties of the object under inspection and the reference detector detects a reference state, and
wherein the coil is wound to surround a surface property inspection region of the object under inspection, and an eddy current is excited in the surface property inspection region by supplying AC power to the coil.

2. The surface property inspection apparatus of claim 1, wherein the surface property inspection apparatus is built into a surface treatment apparatus for performing shot-peening as the surface processing; and
the surface property inspection apparatus is furnished with a moving mechanism for positioning the object under inspection at an evaluation position, being the inside of the coil of the inspection detector, by conveying and moving the object under inspection or the inspection detector.

3. The surface property inspection apparatus of claim 1, further comprising a first transport mechanism, whereby the object under inspection is drivable up or down, and the object under inspection is transported to an evaluation position inside the inspection detector coil and to a position either above or below said evaluation position, or both; and
a registration portion for registering the object under inspection at a position within a horizontal plane;
whereby surface properties of the object under inspection are evaluated either in-line or out-line in a surface processing step by a shot-peening apparatus for performing shot-peening as surface processing.

4. The surface property inspection apparatus of claim 2, wherein the inspection detector is configured to excite an eddy current in an object under inspection furnished with a gear portion.

5. The surface property inspection apparatus of claim 4, further comprising a magnetic shield disposed on the outside of the coil so as to surround the object under inspection, blocking off external magnetism.

6. The surface property inspection apparatus of claim 5, further comprising a temperature sensor for measuring the temperature of the surface of the object under inspection; and wherein the evaluation apparatus makes a pass/fail judgment of the surface processing state of the object under inspection if the temperature detected by the temperature sensor is within a predetermined range, and does not make a pass/fail judgment of the surface processing state of the object under inspection if the temperature detected by the temperature sensor is outside the predetermined range.

7. A surface processing apparatus, comprising the surface property inspection apparatus of claim 2, and a holding portion for holding the object under inspection in a registered state, the surface processing apparatus performing shot-peening as the surface processing, wherein the object under inspection held by the holding portion is positioned at an evaluation position inside the coil of the inspection detector by transporting and moving the object under inspection held by the holding portion or the inspection detector, and the surface property inspection apparatus inspects the surface properties of the object under inspection before and after shot-peening or after shot-peening.

8. A surface processing system, comprising:

the surface property inspection apparatus of claim 3;

a surface processing apparatus for performing shot-peening as the surface processing;

a second transport mechanism for transporting the object under inspection moved to a first standby position by the first transport mechanism in a horizontal direction or a direction inclined relative to the horizontal direction and for transporting the object under inspection up to a predetermined position on the surface processing apparatus; and a third transport mechanism capable of transporting the object under inspection in a horizontal direction or a direction inclined relative to the horizontal direction, and of transporting the object under inspection from a pre-shot-peening area via a second standby position to a shot-peening and inspection-completed area;

whereby the first standby position is a position above or below the evaluation position and facing the surface processing position;

the second standby position is the evaluation position or a position above or below the evaluation position;

the third transport mechanism transports the object under inspection from the pre-shot-peening area up to the second standby position; and by movement of at least one of either the object under inspection or the inspection detector, transported to the second standby position, the object under inspection is positioned in the evaluation position of the inspection detector; and the third transport mechanism transports an object under inspection moved to the second standby position by the first transport mechanism to the shot-peening and inspection-completed area.

9. The surface processing system of claim 8, further comprising an inspection detector transport mechanism for moving the inspection detector up and down;

whereby the second standby position is the evaluation position; and when the object under inspection is transported as far as the second standby position, the object under inspection is positioned at the evaluation position of the inspection detector by the movement of the inspection detector up or down by the inspection detector transport mechanism.

10. The surface processing system of claim 8, wherein the second standby position is a position either above or below the evaluation position; and an object under inspection transported as far as the second standby position is positioned at the evaluation position of the inspection detector by being moved up or down by the first transport mechanism.

11. A surface property inspection method, comprising steps of:

a providing step for providing the surface property inspection apparatus of claim 1;

a disposition step for disposing the inspection detector so that an eddy current is excited in the object under inspection by supplying AC power from the AC power supply to the AC bridge circuit; and an evaluation step for evaluating the surface properties of the object under inspection based on the output signal output from the AC bridge circuit.

12. The surface property inspection method of claim 11, further comprising a step for preparing and measuring a reference inspection piece in order to output a reference output for detecting a reference state in the reference detector.

13. The surface property inspection method of claim 11, wherein a reference inspection piece is not used to output a reference output for detecting a reference state in the reference detector.

14. The surface property inspection method of claim 13, wherein the surface properties of the object under inspection are respectively measured before and after surface processing, and a pass/fail judgment of the surface processing state of the object under inspection is made by comparing the respective measured values.

15. The surface property inspection apparatus claim 1, in which the reference detector has a coil and a ferromagnetic core disposed on the inside of this coil, in which an eddy current is excited by supplying AC power to the coil.

16. The surface property inspection apparatus of claim 15, wherein the AC bridge circuit is furnished with a printed circuit board, and the variable resistor and the reference detector are disposed on this printed circuit board.

17. The surface property inspection apparatus of claim 3, wherein the inspection detector is configured to excite an eddy current in an object under inspection furnished with a gear portion.

18. The surface property inspection apparatus of claim 17, further comprising a magnetic shield disposed on the outside of the coil so as to surround the object under inspection, blocking off external magnetism.

19. The surface property inspection apparatus of claim 18, further comprising a temperature sensor for measuring the temperature of the surface of the object under inspection; and wherein the evaluation apparatus makes a pass/fail judgment of the surface processing state of the object under inspection if the temperature detected by the temperature sensor is within a predetermined range, and does not make a pass/fail judgment of the surface processing state of the object under inspection if the temperature detected by the temperature sensor is outside the predetermined range.

* * * * *